(12) United States Patent
Weihua

(10) Patent No.: US 9,770,482 B2
(45) Date of Patent: Sep. 26, 2017

(54) TARGETING THE EGFR-SGLT1 INTERACTION FOR CANCER THERAPY

(71) Applicant: The University of Houston System, Houston, TX (US)

(72) Inventor: Zhang Weihua, Houston, TX (US)

(73) Assignee: The University of Houston System, Houston, TX (US)

( * ) Notice: Subject to any disclaimer, the term of this patent is extended or adjusted under 35 U.S.C. 154(b) by 0 days.

(21) Appl. No.: 15/139,066

(22) Filed: Apr. 26, 2016

(65) Prior Publication Data

US 2016/0228495 A1 Aug. 11, 2016

Related U.S. Application Data

(62) Division of application No. 14/273,375, filed on May 8, 2014, now Pat. No. 9,334,307.

(60) Provisional application No. 61/821,028, filed on May 8, 2013.

(51) Int. Cl.

| | |
|---|---|
| *A61K 38/10* | (2006.01) |
| *A61K 31/517* | (2006.01) |
| *A61K 31/519* | (2006.01) |
| *A61K 31/5377* | (2006.01) |
| *C07K 7/08* | (2006.01) |
| *A61K 45/06* | (2006.01) |
| *A61K 31/7042* | (2006.01) |
| *A61K 31/70* | (2006.01) |
| *A61K 31/422* | (2006.01) |
| *A61K 31/7034* | (2006.01) |
| *A61K 38/17* | (2006.01) |

(52) U.S. Cl.
CPC ............ *A61K 38/10* (2013.01); *A61K 31/422* (2013.01); *A61K 31/517* (2013.01); *A61K 31/519* (2013.01); *A61K 31/5377* (2013.01); *A61K 31/70* (2013.01); *A61K 31/7034* (2013.01); *A61K 31/7042* (2013.01); *A61K 38/179* (2013.01); *A61K 45/06* (2013.01); *C07K 7/08* (2013.01)

(58) Field of Classification Search
None
See application file for complete search history.

(56) References Cited

U.S. PATENT DOCUMENTS

| | | | |
|---|---|---|---|
| 4,840,939 A | 6/1989 | Leveen et al. | |
| 5,595,756 A * | 1/1997 | Bally | ........... A61K 9/1272 264/4.1 |
| 8,703,917 B2 | 4/2014 | Li et al. | |
| 2010/0248249 A1 | 9/2010 | Pronk | |
| 2013/0034558 A1 | 2/2013 | Li | |
| 2013/0085132 A1 | 4/2013 | Miura et al. | |

FOREIGN PATENT DOCUMENTS

| | | |
|---|---|---|
| EP | 0172721 A2 | 2/1986 |
| WO | 0234073 A2 | 5/2002 |
| WO | 2011091716 A1 | 8/2011 |
| WO | 2012174285 A2 | 12/2012 |

OTHER PUBLICATIONS cancer.gov (accessed Jul. 8, 2016).*
Sporn et al. ("Chemoprevention of Cancer," Carcinogenesis, vol. 21 (2000), 525-530).*
Andlauer W et al., "Phloridzin improves absorption of genestin in isolated rat small intestine," Clinical Nutrition, Churchill Livingstone, London, GB, vol. 23, No. 5, Oct. 1, 2004 (Oct. 1, 2004), pp. 989-995, XP004571435, ISSN: 0261-5614, DOI: 10.1016/J.CLNU.2003.11.009.
Takafumi Taguchi et al., "Interactive Effects of Epidermal Growth Factor Receptor (EGFR) and Na+/Glucose Transporter 1 (SGLT-1) Inhibitors on Viability of Adrenocortical Tumor Cells," Endocrine Review vol. 31, Nr. 3, Suppl. 1, Meeting, Meeting Abstract, Presentation No. P1-66, Jun. 19, 2010 (Jun. 19, 2010), XP055344647, Retrieved from the Internet: URL: http://press.endocrine.org/doi/10.1210/endo-meetings.2010.PART1.P2.P1-66 [retrieved on Feb. 10, 2017].
Hynes NE, et al., "ERBB receptors and cancer: the complexity of targeted inhibitors," Nature Reviews Cancer, 5(5):341-354 (2005).
Weiss J., "First line erlotinib for NSCLC patients not selected by EGFR mutation: keep carrying the TORCH or time to let the flame die?" Transl. Lung Cancer Res., 1(3)219-223 (2012).
Cohen SJ, et al., "Phase II and pharmacodynamic study of the farnesyltransferase inhibitor R115777 as initial therapy in patients with metastatic pancreatic adenocarcinoma," J. Clinical Oncology, 21(7):1301-1306 (2003).
Dancey JE, et al., "Targeting epidermal growth factor receptor—are we missing the mark?" Lancet 362(9377):62-64 (2003).
Hernes E., et al., "Expression of the epidermal growth factor receptor family in prostate carcinoma before and during androgen-independence," British J. Cancer, 90(2):449-454 (2004).
Pu Ys, et al., "Epidermal growth factor receptor inhibitor (PD168393) potentiates cytotoxic effects of paclitaxel against androgen-independent prostate cancer cells," Biochemical Pharmacology, 71(6):751-760 (2006).
Sherwood ER, et al., Epidermal growth factor-related peptides and the epidermal growth factor receptor in normal and malignant prostate, World J. Urology, 13(5):290-296 (1995).
Zellweger T., et al., "Expression patterns of potential therapeutic targets in prostate cancer," International J. Cancer, 113(4):619-628 (2005).

(Continued)

*Primary Examiner* — James H Alstrum Acevedo
*Assistant Examiner* — Tara Martinez
(74) *Attorney, Agent, or Firm* — Blank Rome LLP

(57) ABSTRACT

A compound can destabilize an epidermal growth factor receptor (EGFR) protein and a sodium/glucose co-transporter 1 (SGLT 1) protein. In one embodiment, the compound is a peptide derived from the interacting domain of EGFR. In another embodiment, the peptide is administered to a patient to treat cancer.

6 Claims, 15 Drawing Sheets

(56) References Cited

OTHER PUBLICATIONS

Canil CM, et al., "Randomized phase II study of two doses of gefitinib in hormone-refractory prostate cancer: a trial of the National Cancer Institute of Canada—Clinical Trials Group," J. Clinical Oncology, 23(3):455-460 (2005).
Gross M., et al., "A phase II trial of docetaxel and erlotinib as first-line therapy for elderly patients with androgen-independent prostate cancer," BMC Cancer 7:142 (2007).
Threadgill DW, et al., "Targeted disruption of mouse EGF receptor: effect of genetic background on mutant phenotype," Science, 269(5221):230-234 (1995).
Luetteke NC, et al., "The mouse waved-2 phenotype results from a point mutation in the EGF receptor tyrosine kinase," Genes & Development, 8(4):399-413 (1994).
Ewald JA, et al., "Ligand- and kinase activity-independent cell survival mediated by the epidermal growth factor receptor expressed in 32D cells," Experimental Cell Research 282(2)121-131 (2003).
Weihua Z., et al., "Survival of cancer cells is maintained by EGFR independent of its kinase activity," Cancer Cell, 13(5):385-393 (2008).
Wright EM, et al., "Biology of human sodium glucose transporters," Physiological Reviews, 91(2):733-794 (2011).
Castaneda-Sceppa C., et al., "Sodium-dependent glucose transporter protein as a potential therapeutic target for improving glycemic control in diabetes," Nutrition Reviews, 69(12):720-729 (2011).
Hanahan D., et al., "Hallmarks of cancer: the next generation," Cell, 144(5):646-674 (2011).
Ganapathy V., et al., "Nutrient transporters in cancer: relevance to Warburg hypothesis and beyond," Pharmacology & Therapeutics 121(1):29-40 (2009).
Lai B., et al., "Overexpression of SGLT1 is correlated with tumor development and poor prognosis of ovarian carcinoma," Archives of Gynecology and Obstetrics, 285(5):1455-1461 (2012).
Hanabata Y., et al., "Coexpression of SGLT1 and EGFR is associated with tumor differentiation in oral squamous cell carcinoma," Odontology/the Society of the Nippon Dental University, 100(2):156-163 (2012).
Guo GF., et al., "Overexpression of SGLT1 and EGFR in colorectal cancer showing a correlation with the prognosis," Medical Oncology 28 Suppl 1:S197-203 (2011).
Casneuf VF., et al., "Expression of SGLT1, Bcl-2 and p53 in primary pancreatic cancer related to survival," Cancer Investigation 26(8):852-859 (2008).
Blessing A., et al., "Sodium/Glucose Co-transporter 1 Expression Increases in Human Diseased Prostate," J. Cancer. Sci. Ther. 4(9):306-312 (2012).
Lee ST., et al., "PET in prostate and bladder tumors," Seminars in Nuclear Medicine 42(4):231-246 (2012).
Oyama N., et al., "The increased accumulation of [18F]fluorodeoxyglucose in untreated prostate cancer," Japanese J. Clinical Oncology, 29(12):623-629 (1999).
Han L., et al., "High glucose promotes pancreatic cancer cell proliferation via the induction of EGF expression and transactivation of EGFR," Plos One 6(11):e27074 (2011).
Ehrenkranz Jr., et al., "Phlorizin: a review," Diabetes/Metabolism Research and Reviews 21(1):31-38 (2005).
Bazley LA., et al., "The epidermal growth factor receptor family," Endocrine-Related Cancer, 12 Suppl 1:S17-27 (2005).
Xu S., et al., "Loss of EGFR induced autophagy sensitizes hormone refractory prostate cancer cells to adriamycin," The Prostate, 17:1216-1224 (2011).
Ikari A., et al., "Sodium-dependent glucose transporter reduces peroxynitrite and cell injury caused by cisplatin in renal tubular epithelial cells," Biochimica et Biophysica Acta 1717(2):109-117 (2005).
Yu LC., et al., "SGLT-1-mediated glucose uptake protects human intestinal epithelial cells against Giardia duodenalis-induced apoptosis," International journal for parasitology 38(8-9):923-934 (2008).
Huang Shyhmin, et al., "Dual-agent molecular targeting of the epidermal growth factor receptor (EGFR): combining anti-EGFR antibody with tyrosine kinase inhibitor," Cancer Research Aug. 1, 2004, vol. 64, No. 15, Aug. 1, 2004 (Aug. 1, 2004), pp. 5355-5362, XP002762615, ISSN: 0008-5472.
Anonymous, "Unexpected role: EGFR protects cancer cells from starving," EurekAlert! Science News, May 5, 2008 (May 5, 2008), XP55306976, Retrieved from the Internet URL: https://www.eurekalert.org/pub_releases/2008-05/uotm-ure050208.php [retrieved on Sep. 30, 2016].
Chou Chia-Wei, et al. "HDAC Inhibition Decreases the Expression of EGFR in Colorectal Cancer Cells," Plos One, vol. 6, No. 3, Mar. 25, 2011 (Mar. 25, 2011), p. e18087, XP055078579, DOI: 101371/journal.pone.0018087.
Blessing A, et al., "Abstract 989: Profiling the expression of SGLT1 in prostate cancer," Cancer Research, vol. 71, No. 8 Supplement, Apr. 15, 2011 (Apr. 15, 2011), pp. 989-989, XP055307010, US, ISSN: 0008-5472, DOI: 10.1158/1538-7445.AM2011-989.
Partial European Search Report received in corresponding European Patent Application No. 14794114.0, dated Oct. 26, 2016.
Dittmann, et al., "EGFR cooperates with glucose transporter SGLT1 to enable chromatin remodeling in response to ionizing radiation," Radiother Oncol. May 2013, vol. 107(2), p. 247-51, Epub Apr. 17, 2013.
Huber et al., "EGFR-mediated stimulation of sodium/glucose cotransport promotes survival of irradiated human A549 lung adenocarcinoma cells," Radiother Oncol. 2012, vol. 103(3), p. 373-9.
International Search Report and Written Opinion dated Nov. 12, 2014, 16 pgs.

* cited by examiner

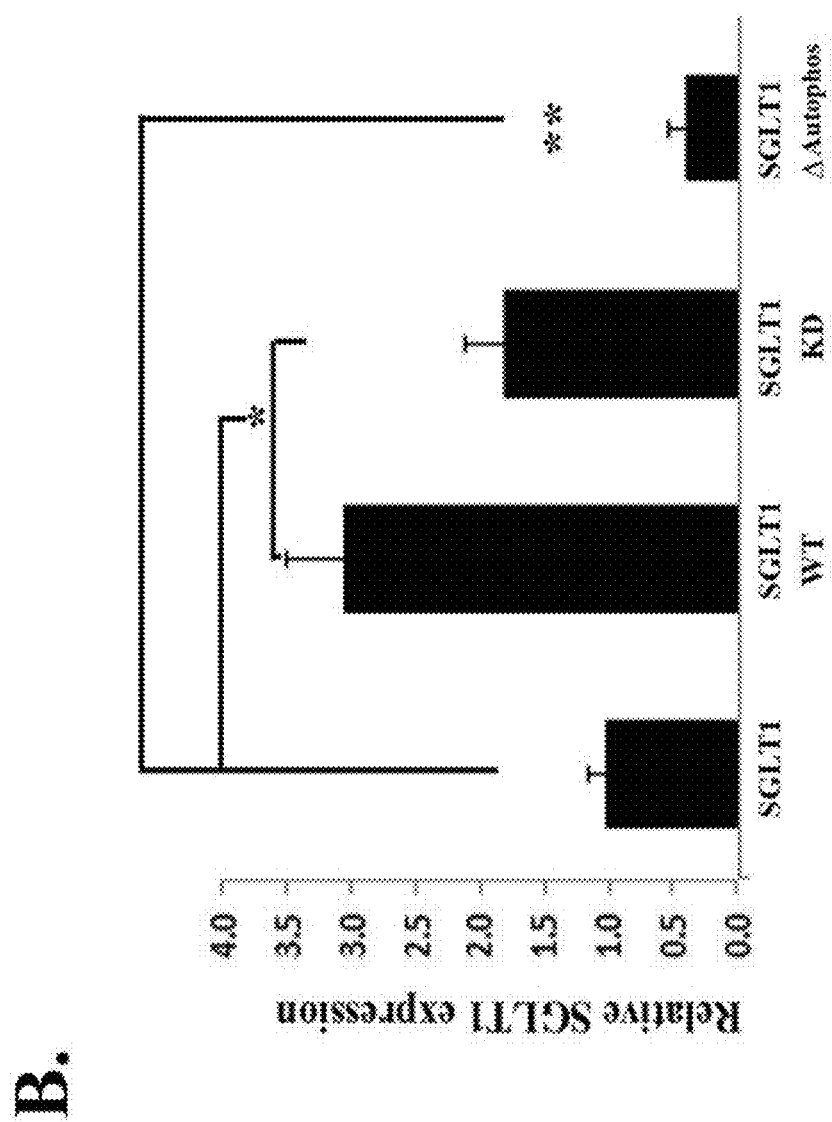

TARGETING THE EGFR-SGLT1 INTERACTION FOR CANCER THERAPY

CROSS-REFERENCES TO RELATED APPLICATIONS

This application is a divisional of U.S. nonprovisional application Ser. No. 14/273,375 filed on May 8, 2014, which claims priority to U.S. provisional application No. 61/821,028 filed on May 8, 2013, both of which are herein incorporated by reference in their entireties.

GOVERNMENT SPONSORSHIP

American Cancer Society (RSG-09-206-01)
Department of Defense Prostate Cancer Research Program (W91ZSQ8334N607)

BACKGROUND

Epidermal growth factor receptor (EGFR) is a receptor tyrosine kinase that is over-active/over-expressed in the majority of cancers of epithelial origin (Hynes N E, et al., *ERBB* receptors and cancer: the complexity of targeted inhibitors, Nature Reviews Cancer, 5(5):341-354 (2005)). Inhibition of the tyrosine kinase activity of EGFR has been the principle strategy of EGFR based cancer therapies. However, targeting EGFR by small molecule inhibitors of receptor tyrosine kinase has not produced satisfactory therapeutic efficacy. The general response rates are between 10-20% across a variety of human malignancies (Weiss J., First line erlotinib for NSCLC patients not selected by EGFR mutation: keep carrying the TORCH or time to let the flame die? Transl. Lung Cancer Res., 1(3):219-223 (2012); Cohen S J, et al., Phase II and pharmacodynamic study of the farnesyltransferase inhibitor R115777 as initial therapy in patients with metastatic pancreatic adenocarcinoma, J. Clinical Oncology, 21(7):1301-1306 (2003); Dancey J E, et al., Targeting epidermal growth factor receptor—are we missing the mark?, Lancet 362(9377):62-64 (2003)). In other words, there is major population of cancer patients that do not respond to EGFR tyrosine kinase inhibitors. For example, although EGFR is over-expressed in more than 80% of late stage prostate cancers and negatively correlates with prognosis, prostate cancer is resistant to EGFR inhibitors (Hernes E., et al., Expression of the epidermal growth factor receptor family in prostate carcinoma before and during androgen-independence, British J. Cancer, 90(2):449-454 (2004); Pu Y S, et al., Epidermal growth factor receptor inhibitor (PD168393) potentiates cytotoxic effects of paclitaxel against androgen-independent prostate cancer cells, Biochemical Pharmacology, 71(6):751-760 (2006); Sherwood E R, et al., Epidermal growth factor-related peptides and the epidermal growth factor receptor in normal and malignant prostate, World J. Urology, 13(5):290-296 (1995); Zellweger T., et al., Expression patterns of potential therapeutic targets in prostate cancer, International J. Cancer, 113(4):619-628 (2005); Canil C M, et al., Randomized phase II study of two doses of gefitinib in hormone-refractory prostate cancer: a trial of the National Cancer Institute of Canada—Clinical Trials Group, J. Clinical Oncology, 23(3):455-460 (2005); Gross M, et al., A phase II trial of docetaxel and erlotinib as first-line therapy for elderly patients with androgen-independent prostate cancer, BMC Cancer 7:142 (2007)).

Evidence indicates that EGFR possesses tyrosine kinase independent functions. For example, EGFR knockout animals die soon after birth (Threadgill D W, et al., Targeted disruption of mouse EGF receptor: effect of genetic background on mutant phenotype, Science, 269(5221):230-234 (1995). However, mice with severely compromised EGFR tyrosine kinase activity are completely viable and display only some epithelial defects (Luetteke N C, et al., The mouse waved-2 phenotype results from a point mutation in the EGF receptor tyrosine kinase, Genes & Development, 8(4):399-413 (1994)). As another example, both a wild type and a kinase-dead EGFR enhanced the survival of EGFR negative 32D hematopoietic cells (Ewald J A, et al., Ligand- and kinase activity-independent cell survival mediated by the epidermal growth factor receptor expressed in 32D cells, Experimental Cell Research 282(2):121-131 (2003). It has also been discovered that EGFR participates in the maintenance of basal intracellular glucose level of cancer cells by interacting with and stabilizing the sodium-glucose cotransporter 1 (SGLT1), independent of EGFR tyrosine kinase activity (Weihua Z, et al., Survival of cancer cells is maintained by EGFR independent of its kinase activity, Cancer Cell, 13(5):385-393 (2008)).

SGLT1 is an active glucose transporter that relies on extracellular sodium concentration to transport glucose into cells independent of glucose concentration (Wright E M, et al., Biology of human sodium glucose transporters, Physiological Reviews, 91(2):733-794 (2011). SGLT1 plays a critical role in glucose absorption and retention in the body (Castaneda-Sceppa C, et al., Sodium-dependent glucose transporter protein as a potential therapeutic target for improving glycemic control in diabetes, Nutrition Reviews, 69(12):720-729 (2011)). One of the hallmarks of cancer is that cancer cells exhibit altered energy metabolism, i.e. cancer cells consume a substantially higher amount of nutrients and energy substrates than their normal counterparts (Hanahan D, et al., Hallmarks of cancer: the next generation, Cell, 144(5):646-674 (2011). This enhanced energy consumption demands a high rate of nutrients uptake, which is achieved by over-expression of plasma membrane transporters (Ganapathy V, et al., Nutrient transporters in cancer: relevance to Warburg hypothesis and beyond, Pharmacology & Therapeutics 121(1):29-40 (2009). Studies have found that SGLT1 is over-expressed in various types of cancers including ovarian carcinoma, oral squamous cell carcinoma, colorectal cancer, pancreatic cancer, and prostate cancer (Lai B, et al., Overexpression of SGLT1 is correlated with tumor development and poor prognosis of ovarian carcinoma, Archives of Gynecology and Obstetrics, 285(5):1455-1461 (2012); Hanabata Y, et al., Coexpression of SGLT1 and EGFR is associated with tumor differentiation in oral squamous cell carcinoma, Odontology/the Society of the Nippon Dental University, 100(2):156-163 (2012); Guo G F, et al., Overexpression of SGLT1 and EGFR in colorectal cancer showing a correlation with the prognosis, Medical Oncology 28 Suppl 1:S197-203 (2011); Casneuf V F, et al., Expression of SGLT1, Bcl-2 and p53 in primary pancreatic cancer related to survival, Cancer Investigation 26(8):852-859 (2008); Blessing A, et al., Sodium/Glucose Co-transporter 1 Expression Increases in Human Diseased Prostate, J. Cancer Sci. Ther. 4(9):306-312 (2012). As an example, late stage prostate cancers express elevated levels of EGFR and uptake a high amount of glucose (Hernes E., et al., Expression of the epidermal growth factor receptor family in prostate carcinoma before and during androgen-independence, British J. Cancer, 90(2):449-454 (2004); Pu Y S, et al., Epidermal growth factor receptor inhibitor (PD168393) potentiates cytotoxic effects of paclitaxel against androgen-independent prostate cancer cells, Biochemical Pharmacology, 71(6):751-760 (2006); Sherwood E R, et al., Epidermal growth factor-related peptides and the epidermal growth factor receptor in normal and malignant prostate, World J. Urology, 13(5):290-296 (1995); Lee S T, et al., PET in prostate and bladder tumors, Seminars in Nuclear Medicine 42(4):231-246 (2012); Oyama N, et al., The increased accumulation of [18F]fluorodeoxyglucose in untreated prostate cancer, Japanese J. Clinical Oncology, 29(12):623-629 (1999)). A better understanding of the functional relationship between EGFR and SGLT1 may lead to identification of novel therapeutic targets for cancer therapy.

Thus, there is need in the art for methods and compositions that can adequately treat cancer cells resistant to EGFR tyrosine kinase inhibitors.

BRIEF DESCRIPTION OF THE DRAWINGS

The foregoing summary, as well as the following detailed description, will be better understood when read in conjunction with the appended drawings. For the purpose of illustration only, there is shown in the drawings certain embodiments. It's understood, however, that the inventive concepts disclosed herein are not limited to the precise arrangements and instrumentalities shown in the figures.

FIG. 2B illustrates a densitometric quantification of bands in the Western blot of FIG. 2A, in accordance with embodiments.

SUMMARY

Figure 1A:
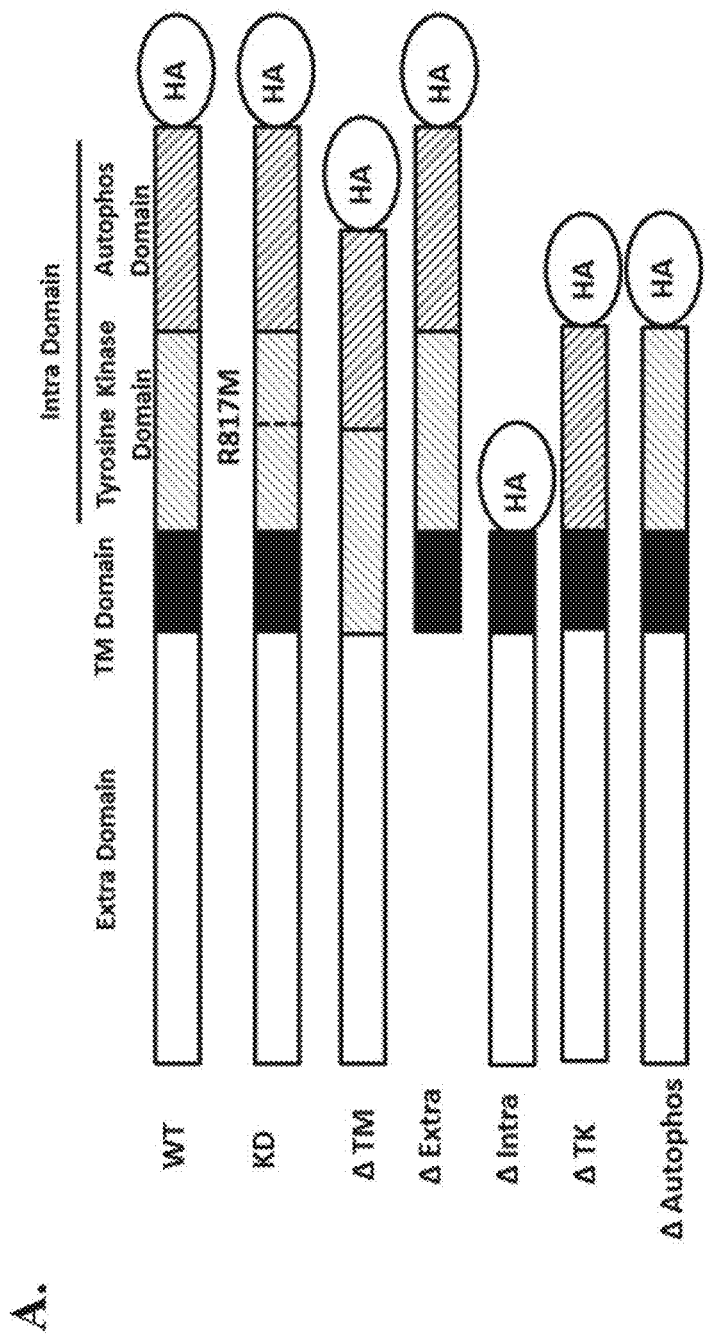
FIG. 1A illustrates a schematic diagram of different constructs of human EGFR, in accordance with embodiments.

A summary of certain embodiments disclosed herein is set forth below. It's understood that this section is presented merely to provide the reader with a brief summary of certain embodiments and that these descriptions are not intended to limit this application's scope. Indeed, this disclosure may encompass a variety of embodiments that may not be set forthherein.

The present application discloses methods and compositions for treating cancer. In one embodiment, a compound destabilizes a binding interaction between an epidermal growth factor receptor (EGFR) and a sodium/glucose co-transporter 1 (SGLT 1). In another embodiment, the compound is a Phlorizin-like compound or a peptide derived from the interacting domain of EGFR.

In an embodiment, a compound that destabilizes the binding interaction between EGFR and SGLT 1 is administered to a subject intratumorally, intravenously, or systemically. The compound may be a Phlorizin-like compound or a peptide derived from the interacting domain of EGFR. In yet another embodiment, the compound may be administered in conjunction with a tyrosine-kinase inhibitor.

DETAILED DESCRIPTION

Before explaining at least one embodiment in detail, it should be understood that the inventive concepts set forth herein are not limited in their application to the construction details or component arrangements set forth in the following description or illustrated in the drawings. It should also be understood that the phraseology and terminology employed herein are merely for descriptive purposes and should not be considered limiting.

It should further be understood that any one of the described features may be used separately or in combination with other features. Other invented systems, methods, features, and advantages will be or become apparent to one with skill in the art upon examining the drawings and the detailed description herein. It's intended that all such additional systems, methods, features, and advantages be protected by the accompanying claims.

All references cited in this application are incorporated by reference in their entirety.

Over-expression of epidermal growth factor receptor (EGFR) is associated with poor prognosis in malignant tumors. Sodium/glucose co-transporter 1 (SGLT1) is an active glucose transporter that is over-expressed in cancers including prostate cancer. It has been found that EGFR interacts with and stabilizes SGLT1 in cancer cells.

As explained in extensive detail below, the following embodiments have been identified in this application:
  the critical micro-domain of EGFR that is required for its
    sufficient interaction with and mutual stabilization with
    SGLT1;
  the effects of activation/inactivation of EGFR on EGFR-
    SGLT1 interaction;
  the measured expression of EGFR and SGLT1 in prostate
    cancer tissues and cell lines;
  the effect of inhibition of SGLT1 on the sensitivity of
    prostate cancer cells to EGFR tyrosine inhibitors;

the amino acid sequence of a synthesized peptide, ESD-01;

the effect of ESD-01 on the stability of EGFR and SGLT1 proteins in cancer cells; and the effects of ESD-01 on survivability of non-cancer cells (HEK293) and several types of cancer cells cultured in vitro.

the ESD-01 peptide made of either L-amino acids or D-amino acids are equally effective in killing cancer cells in vitro.

In one embodiment, the autophosphorylation region (978-1210 amino acids) of EGFR is required for its sufficient interaction with SGLT1. This interaction is independent of EGFR's tyrosine kinase activity. Most importantly, in another embodiment, the EGFR-SGLT1 interaction is irresponsive to EGFR tyrosine kinase modulators (EGF and tyrosine kinase inhibitors). In yet another embodiment, EGFR and SGLT1 co-localize in prostate cancer tissues. In still another embodiment, inhibition of SGLT1 by a SGLT1 inhibitor (Phlorizin) sensitizes prostate cancer cells (PC3 and LNCaP) to EGFR inhibitors (Gefitnib and Erlotinib). In a further embodiment, ESD-01 (SEQ ID NO: 001) destabilizes the EGFR-SGLT1 interaction. All of this data suggests that EGFR in cancer cells can exit in two types of statuses—a tyrosine kinase modulator responsive status and an irresponsive status. Therefore, in an embodiment, SGLT1 is a protein involved in EGFR's functions that are irresponsive to EGFR tyrosine kinase inhibitors, and the EGFR-SGLT1 interaction may be a novel target for prostate cancer therapy.

EGFR Protein Region Required for Interaction with SGLT1

In one embodiment, to determine the EGFR protein region required for its interaction with SGLT1, a flag tagged SGLT1[23] and HA tagged EGFRs having a variety of mutations may be created (Blessing A, et al., Sodium/Glucose Co-transporter 1 Expression Increases in Human Diseased Prostate, J. Cancer Sci. Ther. 4(9):306-312 (2012)). FIG. 1A, by way of example only, illustrates a schematic diagram of human EGFR constructs that may be used to determine the EGFR protein region required for its interaction with SGLT1. For example, in some embodiments, the constructs may include: wild type EGFR ("WT"); kinase dead EGFR (R817M) ("KD") (SEQ ID NO: 012); transmembrane domain deletion (645-670aa) ("ΔTM") (SEQ ID NO: 013); extracellular domain deletion (1-644aa) ("ΔExtra") (SEQ ID NO: 014); intracellular domain deletion (671-1210aa) ("ΔIntra") (SEQ ID NO: 015); tyrosine kinase domain deletion (670-977aa) ("ΔTK") (SEQ ID NO: 016); or autophosphorylation domain deletion (978-1210aa) ("ΔAutophos") (SEQ ID NO: 017).

Figure 1B:
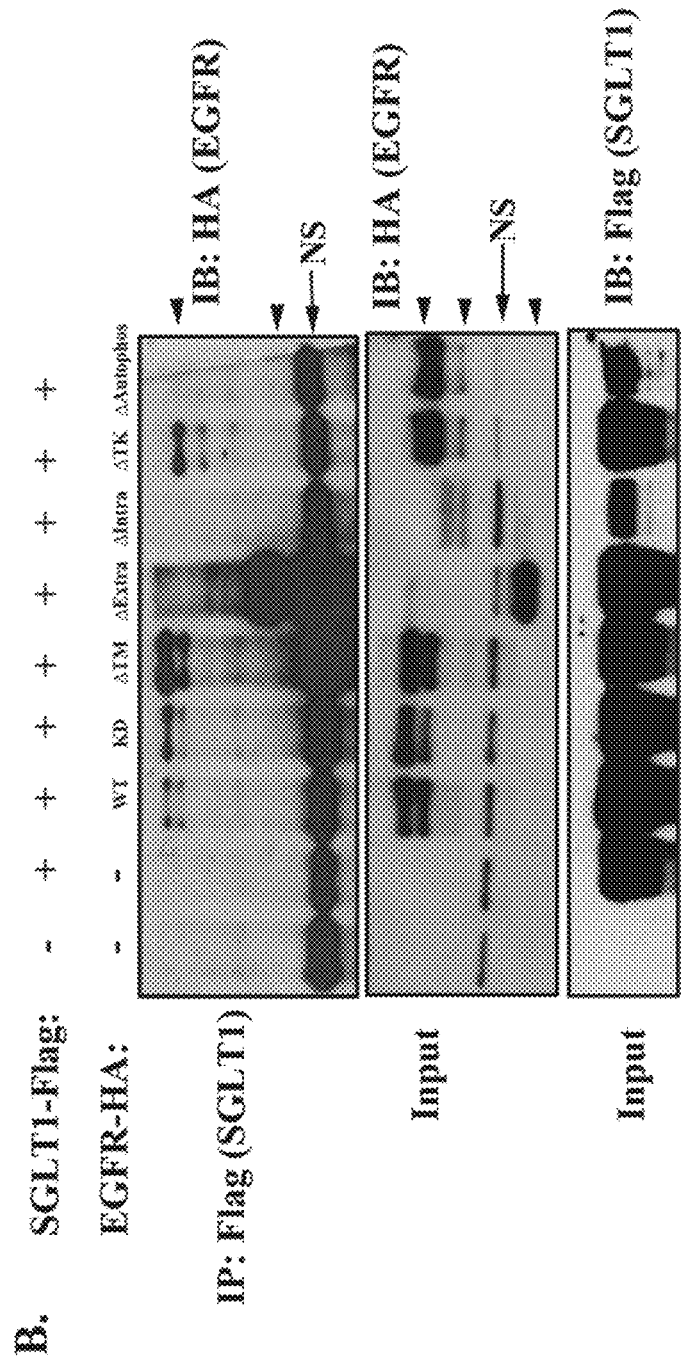
FIG. 1B illustrates an immunoprecipitation coupled Western blot analysis of interactions between mutated EGFRs and SGLT1, in accordance with embodiments.

In an embodiment, the flagged SGLT1 and above identified HA tagged EGFRs can be transiently co-transfected into HEK293 cells. In another embodiment, SGLT1 can be immunoprecipitated using anti-flag antibodies. In yet another embodiment, Western blot analyses may be performed for HA tagged EGFRs. FIG. 1B, by way of example only, illustrates a Western blot analysis of interactions between mutated EGFRs and SGLT1, where IP=immunoprecipitation, IB=Immunoblot, and Input=expression levels of indicated exogenous proteins in HEK293 whole cell lysates used for the immunoprecipitation. As shown in FIG. 1B, deletion of the entire intracellular domain or the autophosphorylation domain of EGFR substantially diminishes its interaction with SGLT1. In one embodiment, the autophosphorylation domain of EGFR is required for its sufficient interaction with SGLT1.

Previously, using EGFR's extracellular domain and an intracellular domain that does not contain the EGFR TM domain, it was discoverred that the extracellular domain of EGFR interacted with SGLT1 better than its intracellular domain (Weihua Z, et al., Survival of cancer cells is maintained by EGFR independent of its kinase activity, Cancer Cell 13(5):385-393 (2008)). In an embodiment, to further characterize the EGFR-SGLT1 interaction at the plasma membrane, the TM domain may be included into the constructs of truncated EGFRs. In one embodiment, the TM containing intracellular domain of EGFR, especially the autophosphorylation domain, interacts more strongly with SGLT1 than its extracelluar domain. The discrepancy between this embodiment and the data shown in the previous report is very likely due to the lack of TM domain in the intracellular domain construct used in the previous study.

Figure 2A:
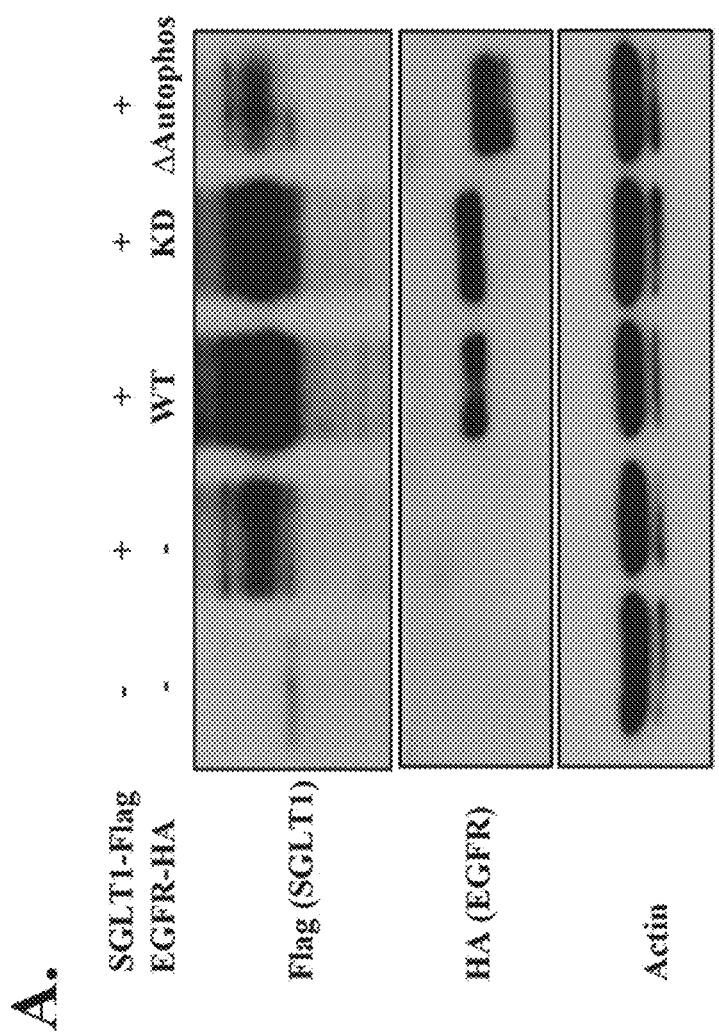
FIG. 2A illustrates a Western blot analysis of expression levels of SGTL1 in HEK293 cells co-transfected with the WT-EGFR, the KD-EGFR and the ΔAutophos-EGFR, in accordance with embodiments.

EGFR's Autophosphorylation Domain Required to Prevent Proteasome-Mediated SGLT1 Degradation In an embodiment, to determine whether the autophosphorylation domain of EGFR is required to sustain the stability of SGLT1, the expression level of SGLT1 co-transfected with the WT-EGFR, the KD-EGFR, and the ΔAutoPhos-EGFR into HEK293 cells may be measured. For example, FIG. 2A, by way of example only, illustrates a Western blot analysis of expression levels of SGTL1 in HEK293 cells co-transfected with the WT-EGFR, the KD-EGFR and the ΔAutophos-EGFR. The same amounts of DNA plasmids of SGLT1 and EGFRs may be used in each group of treatments. Furthermore, control cells can be transfected with the same amount of DNA of the empty vector. Actin may be used as loading control. FIG. 2B, by way of example only, illustrates a densitometric quantification of bands in the Western blot of FIG. 2A. Asterisk marks indicate statistical significance between the linked representative groups from triplicate experiments.

As shown in FIGS. 2A-2B, in one embodiment, the level of SGLT1 in the WT-EGFR and the KD-EGFR transfected cells is much higher than that in the control vector or ΔAutoPhos-EGFR transfected cells. In another embodiment, the autophosphorylation domain of EGFR can maintain the expression level of SGLT1. In still another embodiment, the level of SGLT1 in the ΔAutoPhos-EGFR transfected cells is significantly lower than that of the control cells. In yet another embodiment, the loss of SGLT1 interaction with EGFR can promote down-regulation of SGLT1.

Figure 2C:
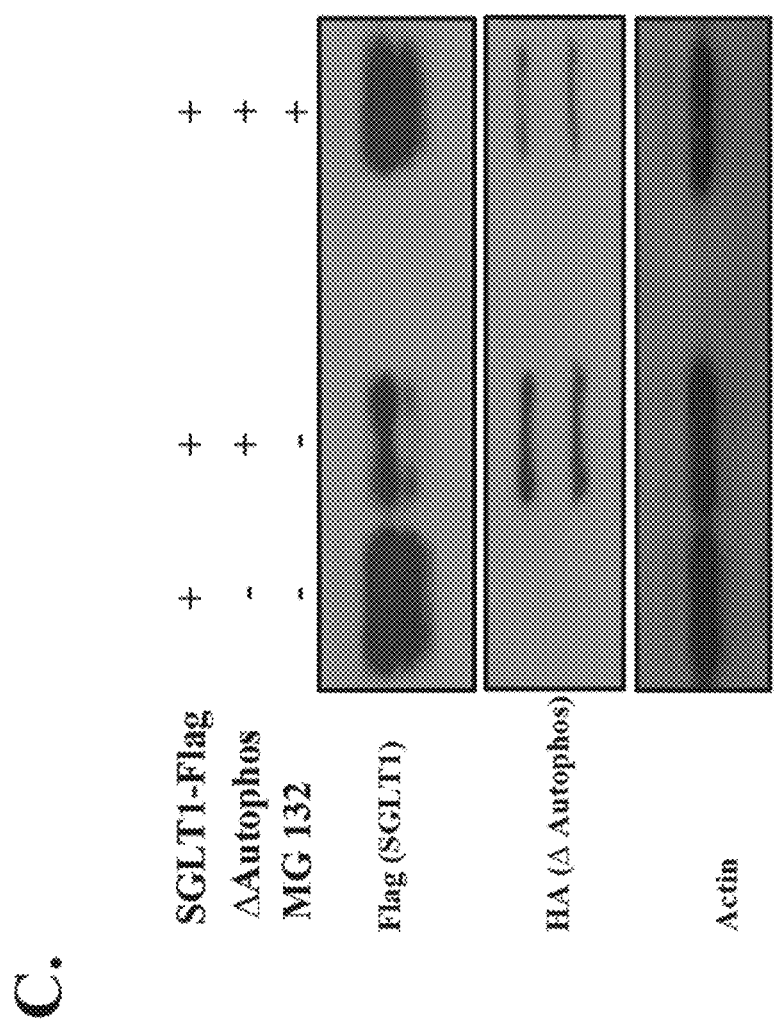
FIG. 2C illustrates a Western blot analysis of the effect of a proteasome inhibitor MG132 on the down-regulation of SGLT1 by ΔAutophos-EGFR, in accordance with embodiments.
Figure 2D:
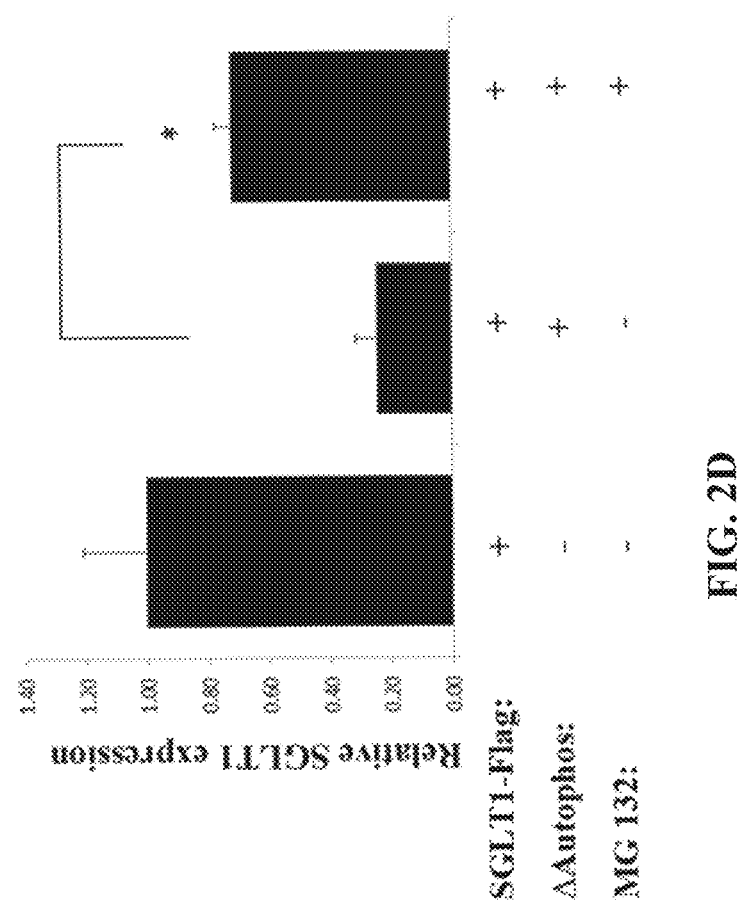
FIG. 2D illustrates a densitometric quantification of bands in the Western blot of FIG. 2C, in accordance with embodiments.

In an embodiment, to determine whether proteasome is involved in loss of interaction with EGFR induced down-regulation of SGLT1, SGLT1 and ΔAutoPhos-EGFR co-transfected HEK293 cells can be treated with a proteasome inhibitor, such as but not limited to MG231. For example, FIG. 2C illustrates a Western blot analysis of the effect of a proteasome inhibitor MG132 on the down-regulation of SGLT1 by ΔAutophos-EGFR. Actin may be used as a loading control. FIG. 2D, by way of example only, illustrates a densitometric quantification of bands in the Western blot of FIG. 2C. Asterisk marks indicate statistical significance between the linked representative groups from triplicate experiments.

As shown in FIGS. 2C-2D, by way of example only, in one embodiment MG231 can inhibit the down-regulation of SGLT1 in ΔAutoPhos-EGFR transfected cells. In another embodiment, the proteasome machinery is involved in the loss of interaction with EGFR induced SGLT1 down-regulation. In other words, proteasomes may cause the ultimate degradation of SGLT1 when the EGFR-SLGT1 interaction is compromised. In yet another embodiment, the proteasome machinery may be a potential therapeutic target alone or in combination with the EGFR-SLGT1 interaction.

In one embodiment, deleting the SGLT1 interacting domain in EGFR promotes the down-regulation of SGTL1 via the proteasome machinery. In another embodiment, this disruption of the EGFR-SGLT1 interaction in EGFR positive cancer cells can lead to down-regulation of SGLT1. Furthermore, previous data shows that knocking down SGLT1 by shRNA results in autophagic cell death of prostate cancer cells (Weihua Z, et al., Survival of cancer cells is maintained by EGFR independent of its kinase activity, Cancer Cell 13(5):385-393 (2008). In an embodiment, the EGFR-SGLT1 interaction can be a significant target to improve EGFR based therapy for cancer.

EGFR-SGLT1 Interaction is Irresponsive to EGFR Tyrosine Kinase Inhibitors

Figure 3A:
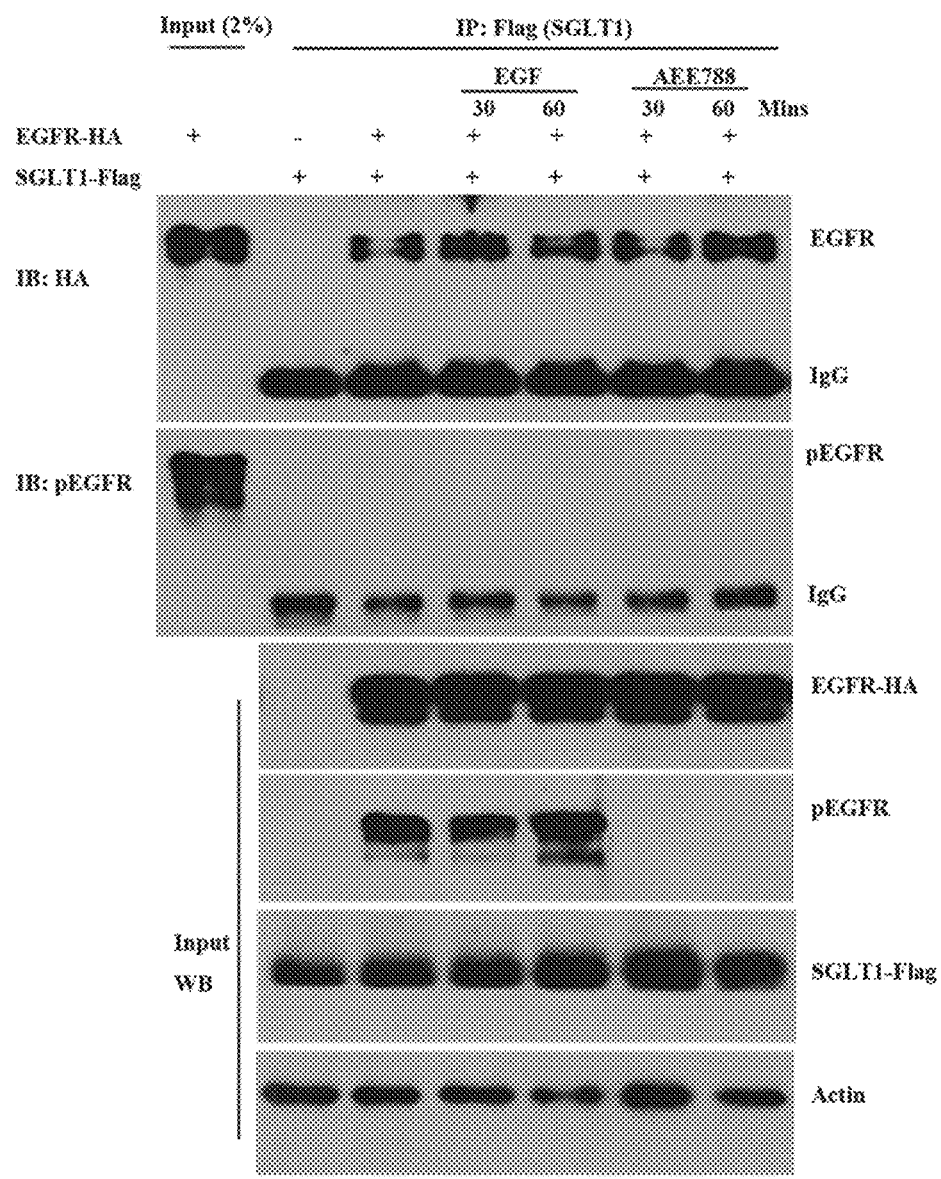
FIG. 3A illustrates an immunoprecipitation coupled Western blot analysis of interactions between EGFR-HA and SGLT1-Flag in HEK293 cells treated with EGF or AEE788, in accordance with embodiments.

In an embodiment, the effects of EGFR tyrosine kinase inhibitors on EGFR's interaction with SGLT1 can be determined. In an embodiment, WT-EGFR and SGLT1 co-transfected HEK293 cells can be treated with either EGF or an EGFR tyrosine kinase inhibitor, AEE788. SGLT1 may be immunoprecipitated, and the levels of EGFR that were co-immunoprecipitated with SGLT1 can be measured. For example, FIG. 3A, by way of example only, illustrates an immunoprecipitation coupled Western blot analysis of interactions between EGFR-HA and SGLT1-Flag in HEK293 cells treated with EGF or AEE788, where EGFR=total EGFR, pEGFR=phosphorylated EGFR, IP=immunoprecipitation, IB=immunoblot, and Input=expression levels of indicated exogenous proteins in HEK293 whole cell lysates used for the immunoprecipitation. As shown in FIG. 3A, in one embodiment, neither EGF nor AEE788 significantly affects the EGFR-SGLT1 interaction. In yet another embodiment, the EGFR that co-precipitates with SGLT1 is not phosphorylated.

Figure 3B:
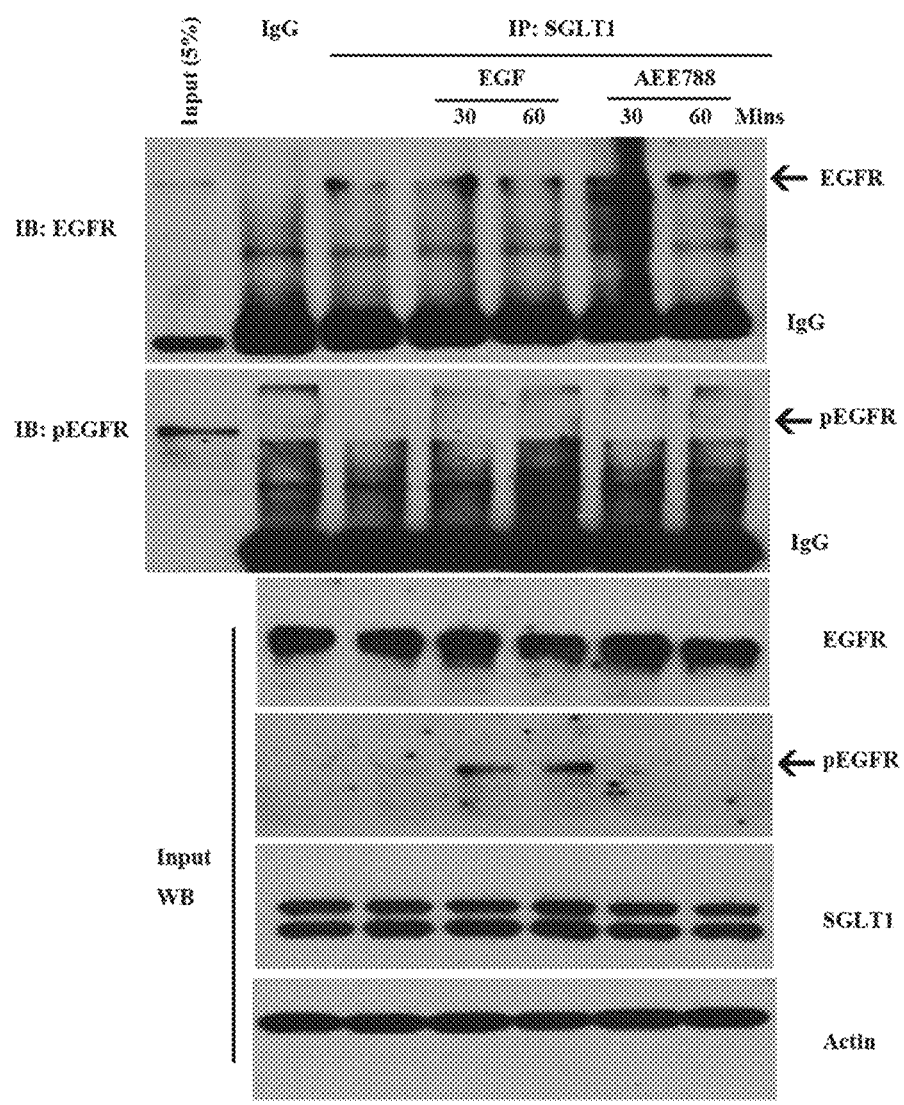
FIG. 3B illustrates immunoprecipitation coupled Western blot analysis of interactions between endogenous EGFR and SGLT1 in PC3 cells treated with EGF or AEE788, in accordance with embodiments.

In one embodiment, to determine the effects of EGF and AEE788 on endogenous EGFR-SGLT1 interaction and the phosphorylation status of endogenous EGFR that interacts with SGLT1, endogenous SGLT1 of PC3 cells treated with EGF or AEE788 may be immunoprecipitated. In another embodiment, the phosphorylation status of the EGFR co-precipitated with SGLT1 can be measured. By way of example only, FIG. 3B illustrates an immunoprecipitation coupled Western blot analysis of interactions between endogenous EGFR and SGLT1 in PC3 cells treated with EGF or AEE788. In an embodiment, neither EGF nor AEE788 affect the EGFR-SGLT1 interaction. In yet another embodiment, the endogenous SGLT1 interacting EGFR is not phosphorylated. In still another embodiment, the EGFR-SGLT1 interaction is irresponsive to modulators of EGFR's tyrosine kinase activity. In yet a further embodiment, EGFR can be targeted for cancer therapy at its non-kinase functionality, including but not limited to its interaction with SGLT1.

It has been well documented that, upon phosphorylation of tyrosines within the autophosphorylation domain of EGFR, the autophosphorylation domain serves as a major docking site for recruitment of adaptor/effector proteins that transactivate downstream signaling (Bazley L A, et al., The epidermal growth factor receptor family, Endocrine-Related Cancer, 12 Suppl 1:S17-27 (2005)). Based on the results of FIG. 3A, in an embodiment, the EGFR-SGLT1 interaction is independent of EGFR activation/inactivation. The autophosphorylation domain of EGFR functions as a protein-protein interacting domain independent of EGFR's tyrosine kinase activity. In one embodiment, EGFR possesses pro-survival functions independent of its tyrosine kinase activity. For example, EGFR can exist in two types of statuses—a tyrosine kinase responsive status and a tyrosine kinase irresponsive status. Upon activation by EGFR's ligands, the autophosphorylation domain of the kinase responsive EGFR can be phosphorylated and can recruit effectors to trigger downstream signals. Alternatively, the kinase irresponsive EGFR may constantly interact with proteins regardless of the presence of EGFR ligands, and regardless of activation or inactivation of its tyrosine kinase. In yet another embodiment, SGLT1 may be one of such proteins that bind to and keep EGFRs in their kinase irresponsive status. In yet another embodiment, the non-phosphorylated autophosphorylation domain of EGFR may be used as a tool for identifying therapeutic targets.

Figure 4A:
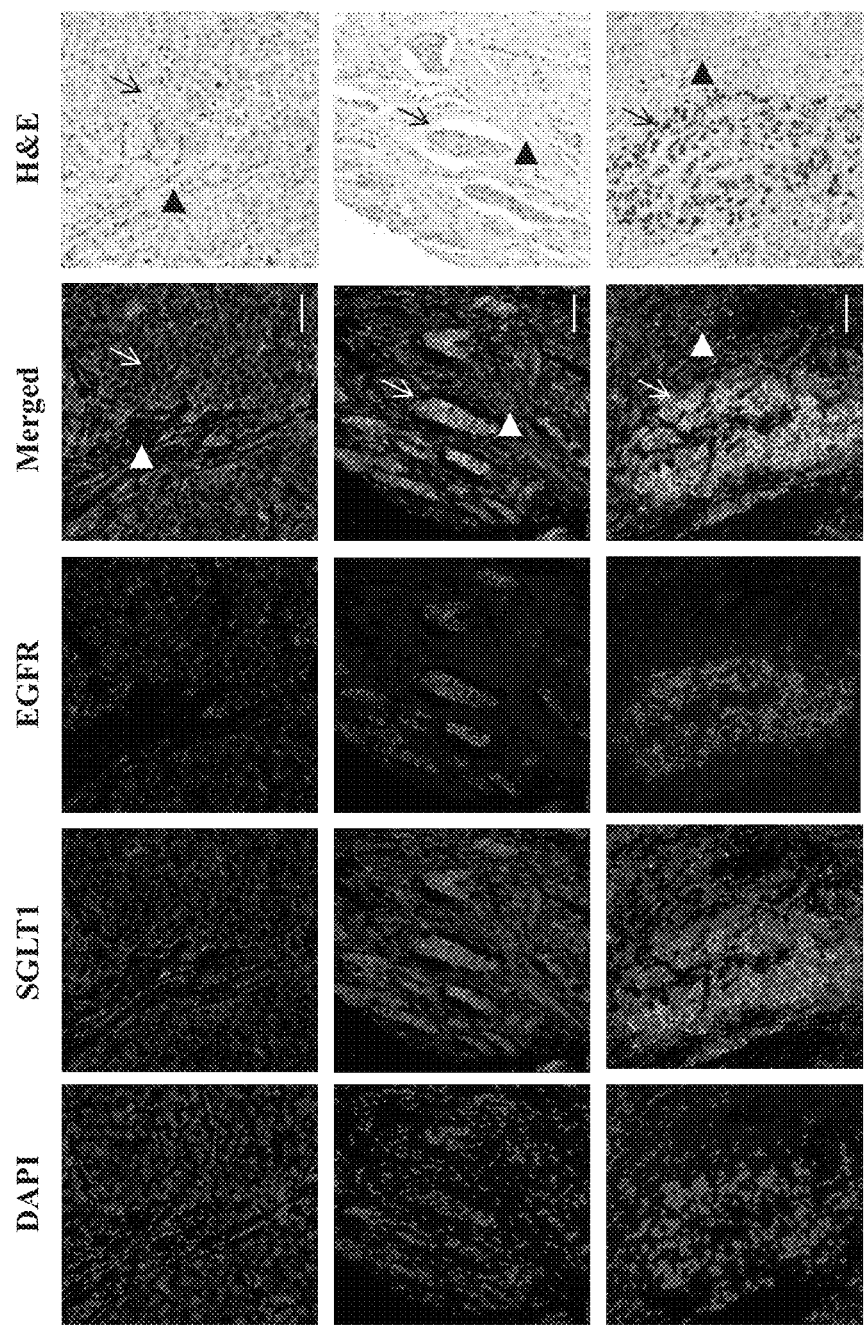
FIG. 4A illustrates co-localization of SGLT1 and EGFR in prostate cancer tissues from a prostate cancer tissue array, in accordance with embodiments.

Inhibition of SGLT1 by SGLT1 Inhibitor Sensitizes Prostate Cancer Cells to EGFR Inhibitors In an embodiment, to determine the clinical relevance of the EGFR-SGLT1 interaction, immunofluorescent co-staining of EGFR and SGLT1 on a tissue microarray of prostate cancers (n=44) may be performed. For example, FIG. 4A, by way of example only, illustrates the results of three representative prostate cancer tissues from a prostate cancer tissue array. In an embodiment, SGLT1 (green) and EGFR (red) may be co-localized in the prostate tissue (e.g., orange or yellow, as indicated by arrows). In another embodiment, stromal cells may be positive for SGLT1, but negative for EGFR (e.g., indicated by arrow heads). In yet another embodiment, in EGFR positive cancer samples (n=41), SGLT1 co-localizes with EGFR in cancer cells, but not stromal cells.

In still another embodiment, the EGFR-SGLT1 interaction may contribute to the pathogenesis of prostate cancer. For example, in an embodiment, the co-localization of EGFR with SGLT1 in prostate cancer tissues can indicate that the EGFR-SGLT1 interaction is cancer relevant. Currently, at the clinic, EGFR tyrosine kinase inhibitors have not yet shown satisfactory therapeutic effects for prostate cancer (Canil C M, et al., Randomized phase II study of two doses of gefitinib in hormone-refractory prostate cancer: a trial of the National Cancer Institute of Canada-Clinical Trials Group, J. Clinical Oncology, 23(3):455-460 (2005); Gross M, et al., A phase II trial of docetaxel and erlotinib as first-line therapy for elderly patients with androgen-independent prostate cancer, BMC Cancer 7:142 (2007)). In one embodiment, considering the fact that EGFR expression correlates with disease progression of prostate cancer and the clinical unresponsiveness of prostate cancers to EGFR tyrosine kinase inhibitors, EGFR may contribute to the disease progression of prostate cancer independent of its tyrosine kinase activity. Additionally, previous findings conclude that (1) prostate cancer tissues have increased expression of SGLT1,[23] (2) a loss of EGFR protein but not its tyrosine kinase activity sensitized prostate cancer cells to chemotherapeutic agent,[29] and (3) a loss of EGFR induced autophagic cell death was mediated by down-regulation of SGLT1 protein (Blessing A, et al., Sodium/Glucose Co-transporter 1 Expression Increases in Human Diseased Prostate, J. Cancer Sci. Ther. 4(9):306-312 (2012); Xu S, et al., Loss of EGFR induced autophagy sensitizes hormone refractory prostate cancer cells to adriamycin, The Prostate. 17:1216-1224 (2011); Weihua Z, et al., Survival of cancer cells is maintained by EGFR independent of its kinase activity, Cancer Cell, 13(5):385-393 (2008)). In yet another embodiment, EGFR can promote prostate cancer progression via stabilizing SGLT1 to sustain the high demand of glucose of late stage cancer cells. This embodiment is not only supported by all the embodiments described herein, but is also supported by past data that over-expression of SGLT1 prevented renal epithelial cells and intestinal epithelial cells from apoptosis (Ikari A, et al., Sodium-dependent glucose transporter reduces peroxynitrite and cell injury caused by cisplatin in renal tubular epithelial cells, Biochimica et Biophysica Acta 1717(2):109-117 (2005); Yu L C, et al., SGLT-1-mediated glucose uptake protects human intestinal epithelial cells against Giardia duodenalis-induced apoptosis, International journal for parasitology 38(8-9):923-934 (2008)).

It is well known that an increase in glucose levels can activate EGFR, that SGLT1 is over-expressed in prostate cancer tissues, and that prostate cancer is resistant to EGFR inhibitors. (Han L, et al., High glucose promotes pancreatic cancer cell proliferation via the induction of EGF expression and transactivation of EGFR, PloS One 6(11):e27074 (2011); Blessing A, et al., Sodium/Glucose Co-transporter 1 Expression Increases in Human Diseased Prostate, J. Cancer Sci. Ther. 4(9):306-312 (2012); Canil C M, et al., Randomized phase II study of two doses of gefitinib in hormone-refractory prostate cancer: a trial of the National Cancer Institute of Canada-Clinical Trials Group, J. Clinical Oncology, 23(3):455-460 (2005); Gross M, et al., A phase II trial of docetaxel and erlotinib as first-line therapy for elderly patients with androgen-independent prostate cancer, BMC Cancer 7:142 (2007)). In an embodiment, SGLT1 and EGFR can synergistically promote prostate cancer growth. In one embodiment, to test whether inhibition of SGLT1 can sensitize prostate cancer cells to EGFR inhibitors, prostate cancer cell lines (e.g., PC3 and LNCaP (both positive for EGFR and SGLT1)), may be treated with EGFR tyrosine kinase inhibitors (e.g., Gefitnib, Erlotinib, Icontinib, Mubritinib, Vandertanib, Lapatinib, Pelitinib, Canertinib, Neratinib, Afatinib and Dacomitinib.) in the presence/absence of an SGLT1 inhibitor (e.g., phlorizin, and phlorizin derivatives, such as Canagliflozin and Dapagliflozin) (Ehrenkranz J R, et al., Phlorizin: a review, Diabetes/Metabolism Research and Reviews 21(1):31-38 (2005)). In one embodiment, the growth inhibitory effects of the treatments may be determined. For example, in an embodiment, cells can be treated with the SGLT1 inhibitor phlorizin (50 µM) with/without EGFR inhibitors (Gefitinib, 10 µM; Erlotinib, 10 µM) for 48 hs before being subjected to MTT assay. The OD value of control cells can be artificially set as 1. All experiments may be repeated for at least 3 times. Asterisk marks indicate statistical significances between linked groups.

Figure 4B:
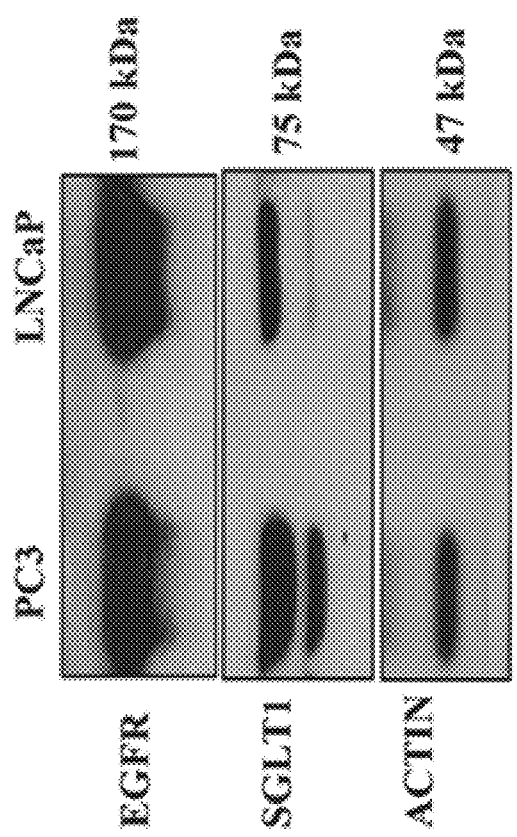
FIG. 4B illustrates a Western blot analysis of expressions of endogenous EGFR and SGLT1 in PC3 and LNCaP cells, in accordance with embodiments.
Figure 4C:
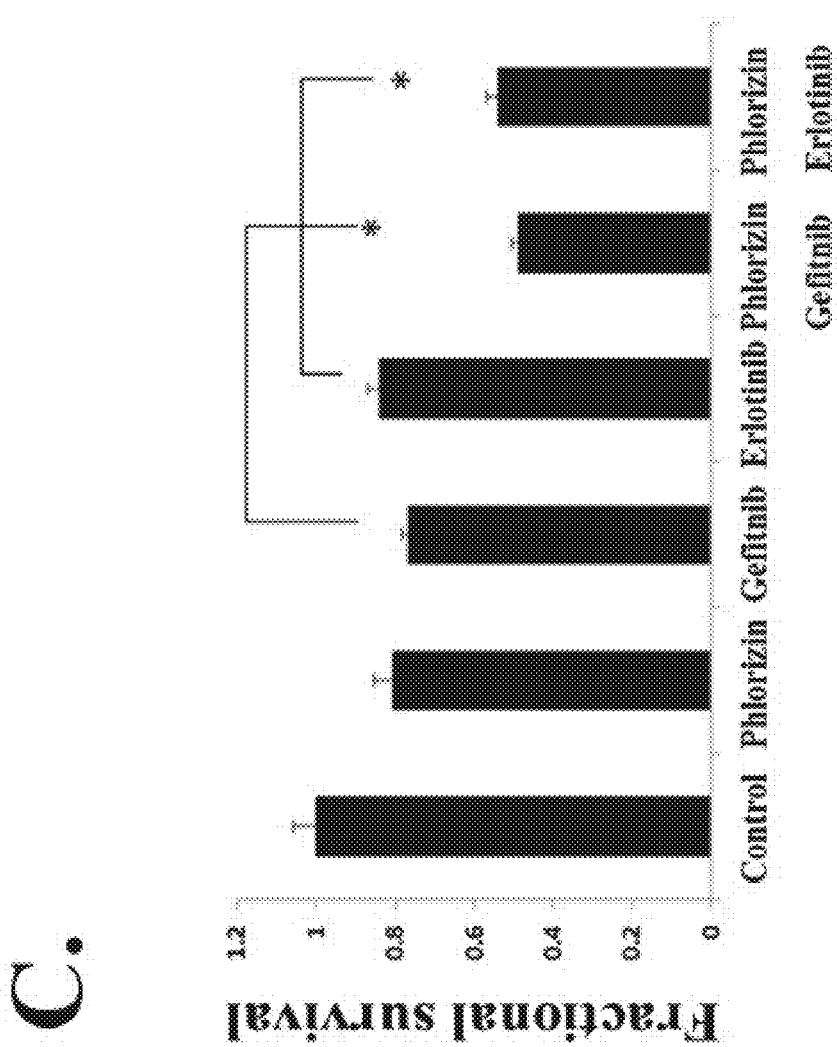
FIG. 4C illustrates an MTT assay showing the effect of inhibition of SGLT1 on the growth inhibitory effect of Gefitinib and Erlotinib on PC3 cells, in accordance with embodiments.
Figure 4D:
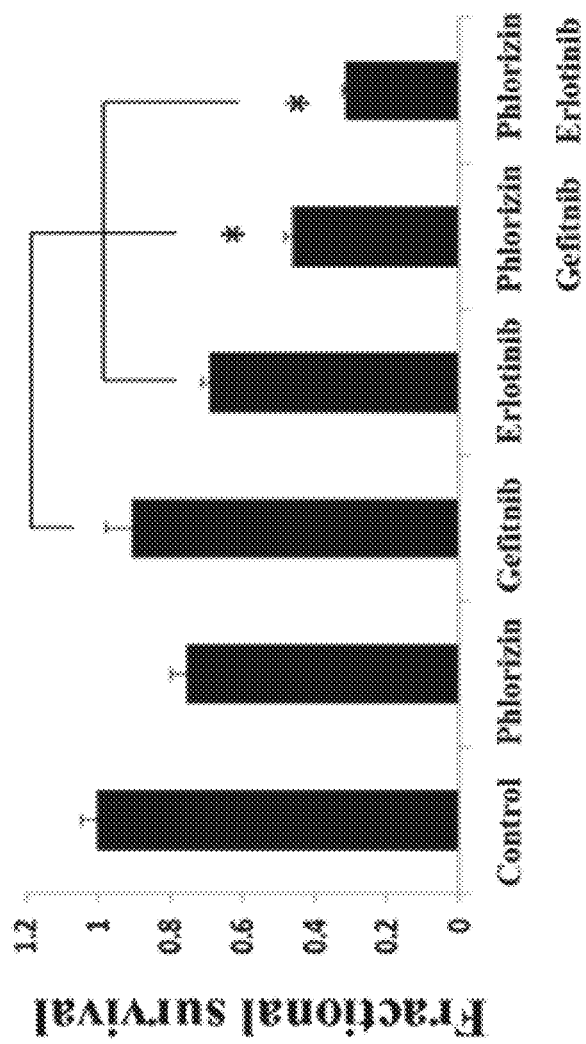
FIG. 4D illustrates an MTT assay showing the effect of inhibition of SGLT1 on the growth inhibitory effect of Gefitinib and Erlotinib on LNCaP cells, in accordance with embodiments.

FIG. 4B, by way of example only, illustrates a Western blot analysis of the expressions of endogenous EGFR and SGLT1 in PC3 and LNCaP cells. In one embodiment, breast and colon cancer cells express EGFR and SGLT1. FIG. 4C shows an MTT assay of the effect of inhibition of SGLT1 on the growth inhibitory effect of Gefitinib and Erlotinib on PC3 cells. FIG. 4D shows an MTT assay of the effect of inhibition of SGLT1 on the growth inhibitory effect of Gefitinib and Erlotinib on LNCaP cells. Based on these results, in one embodiment, co-inhibition of SGLT1 and EGFR functions can more effectively inhibit cancer cell growth. In still another embodiment, Phlorizin can significantly sensitize prostate cancer cells to the growth inhibitory effects of Gefitinib and Erlotinib. In an embodiment, Phlorizin or Phlorizin-like compounds can be administered to a patient, intravenously, intratumorally, or systemically, to treat cancer. In still another embodiment, Phlorizin or Phlorizin-like compounds can be administered to a patient in conjunction with tyrosine-kinase inhibitors to treat cancer.

Figure 5A:
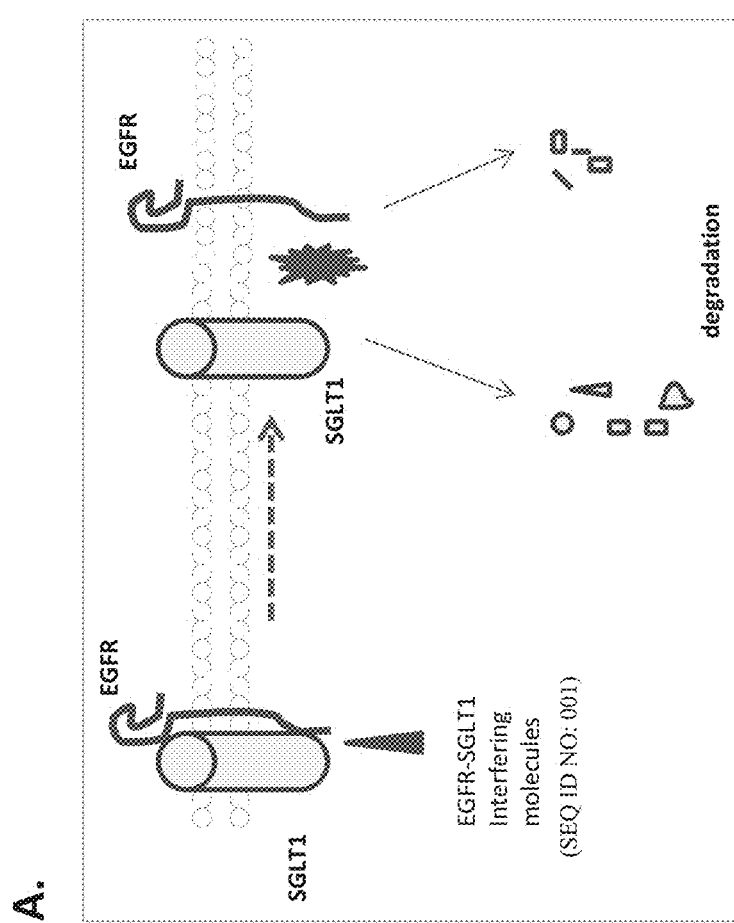
FIG. 5A illustrates disruption of EGFR-SGLT1 interaction by small molecules of peptides to destabilize both proteins, in accordance with embodiments.
Figure 5B:
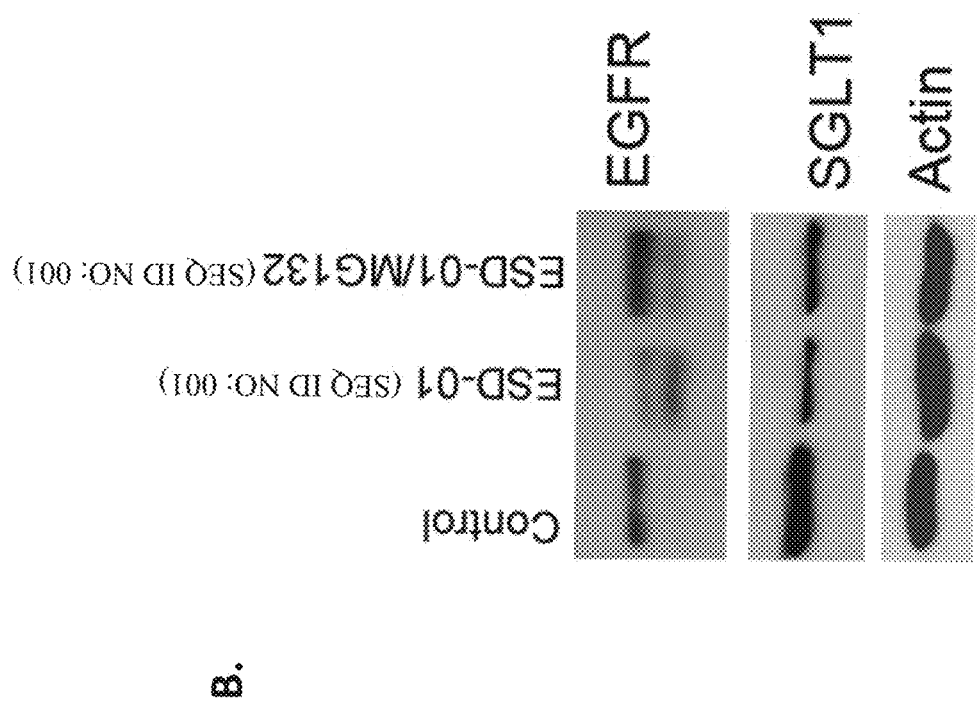
FIG. 5B illustrates that treatment of PC3 cells with an EGFR-SGLT1 disrupting peptide (MTG-01) significantly down-regulates EGFR and SGLT1 proteins, in accordance with embodiments.
Figure 6:
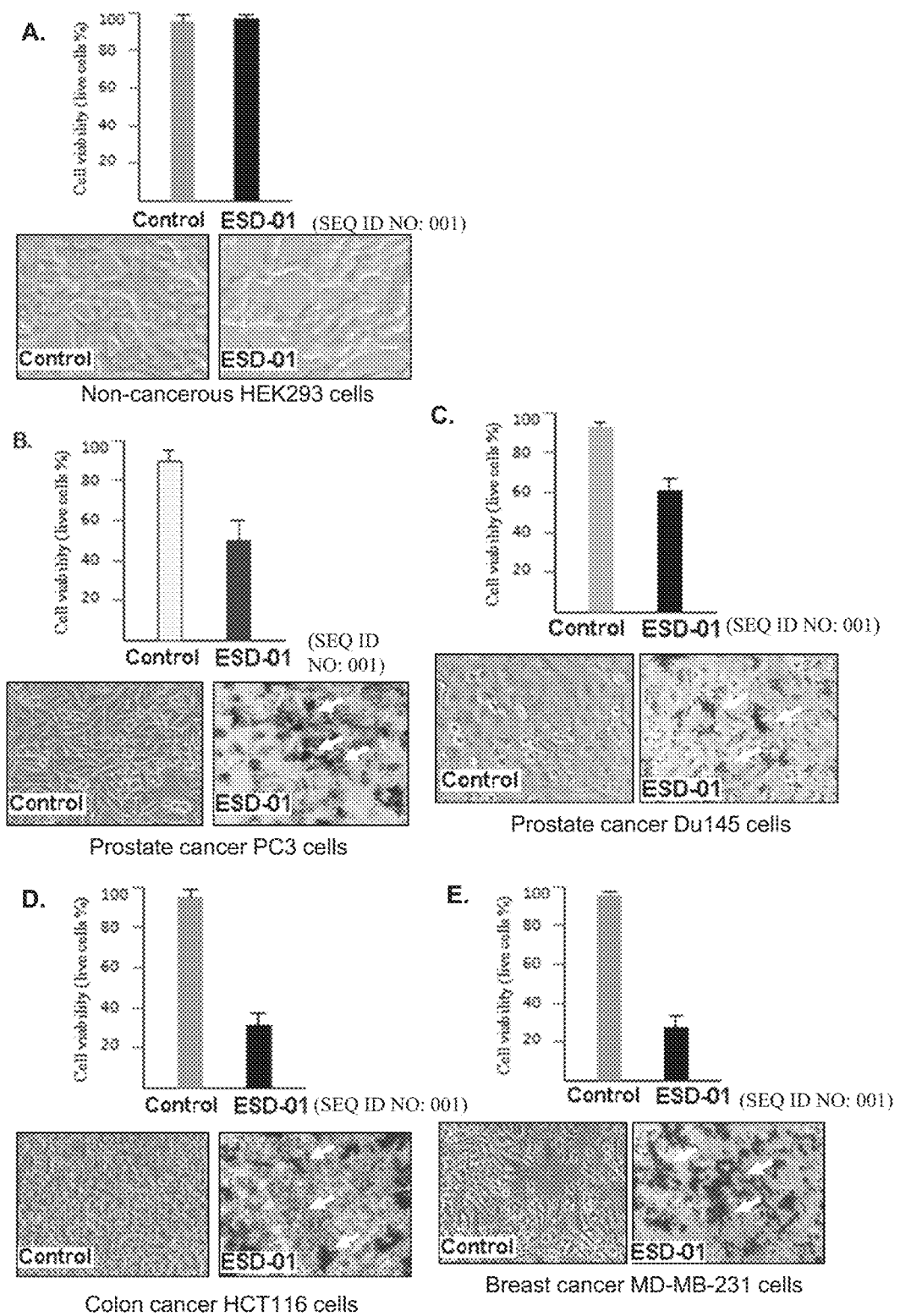
FIG. 6 illustrates the viability of cancerous PC3, Du145, HCT116, and MDA-MB-231 cells and treatment of non-cancerous HEK293 cells when treated with MTG-01, in accordance with embodiments.

In another embodiment, a peptide can destabilize EGFR and SGLT1 proteins of cancer cells. FIG. 5A, by way of example only, illustrates an embodiment of a peptide, called ESD-01 (SEQ ID NO: 001), which can destabilize EGFR and SGLT1 proteins of cancer cells. In one embodiment, the ESD-01 peptide can be selected from the SGLT1 interacting domain of EGFR. In another embodiment, ESD-01 comprises amino acids 1049-1062 of a human EGFR protein (GenBank: AAH94761.1). In still another embodiment, the effects of ESD-01 on the stability of EGFR and SGLT1 in cultured cells (e.g., PC3, MDA-MB-231, and HCT116 cells) can be determined by Western blot analysis. FIG. 5B, by way of example only, shows that ESD-01 treatment (200 µM for 6 hours) significantly down-regulates EGFR and SGLT1 levels in PC3 cells, which are inhibited by the proteasome inhibitor MG132. In an embodiment, inhibition of SGLT1 and EGFR down-regulation by ESD-01 by MG132 suggests that MTG-01 destabilizes EGFR and SGLT1 via proteolysis. In still another embodiment, the effects of ESD-01 on the survivability of cultured cancer cells (e.g, PC3, MDA-MB-231, and HCT116 cells) can be determined by trypan blue uptake assay. FIG. 6, by way of example only, shows that ESD-01 treatment (100 µM for 24 hours) significantly reduces the survivability of a variety of cancer cells including prostate cancer PC3 and Du145 cells, breast cancer MDA-MB-231 cells, and colon cancer HCT116 cells. In yet another embodiment, ESD-01 treatment cannot reduce the survivability of non-cancerous HEK293 cells.

It is well known that replacement of amino acids in a protein/peptide with different amino acids having similar chemical properties can generate proteins/peptides with identical functions. In an embodiment, ESD-01 (SEQ ID NO: 001) can be substituted with amino acids having similar chemical properties or any other mutations that will destabilize EGFR and SGLT1 proteins of cancer cells. For example, in one embodiment, the amino acids can be either L-form or D-form chiral isomers. In another embodiment, Serine (S) in ESD-01 can be substituted with Threonine (T), Tyrosine (Y), or any other non-natural hydroxyl containing amino acid (e.g, SEQ ID NO: 002). In yet another embodiment, Threonine (T) in ESD-01 can be substituted with Serine (S), Tyrosine (Y), or any other non-natural hydroxyl containing amino acid (e.g, SEQ ID NO: 003). In still another embodiment, Lysine (K) in ESD-01 can be substituted with Theronine (T) (e.g, SEQ ID NO: 004). In an embodiment, Glutamine (Q) can in ESD-01 can be substituted with Histidine (H) (e.g., SEQ ID NO: 005). In another embodiment, Threonine (T) at position 10 of ESD-01 can be substituted with Alanine (A) (e.g, SEQ ID NO: 006). In yet another embodiment, where the Serine (S) at position 12 of ESD-01 can be substituted with Leucine (L) (e.g, SEQ ID NO: 007). In still another embodiment, the polar positive charged amino acids in ESD-01, Lysine (K) and Histidine (H), can be any other natural and non-natural positively charged amino acid (e.g., SEQ ID NO: 008). In one embodiment, the polar amino acids in ESD-01, Glutamine (Q) and Cysteine (C), can be any other natural and non-natural polar amino acid (e.g., SEQ ID NO: 009). In another embodiment, the Cysteine (C) in ESD-01 can be any other natural and non-natural thiol side chain (—SH) containing amino acid (e.g., SEQ ID NO: 010). In still another embodiment, the nonpolar amino acids in ESD-01, Leucine (L), Valine (V), and Tryptophan (W), can be any other natural and non-natural nonpolar amino acids (e.g., SEQ ID NO: 011).

It's understood that the above description is intended to be illustrative, and not restrictive. The material has been presented to enable any person skilled in the art to make and use the inventive concepts described herein, and is provided in the context of particular embodiments, variations of which will be readily apparent to those skilled in the art (e.g., some of the disclosed embodiments may be used in combination with each other). Many other embodiments will be apparent to those of skill in the art upon reviewing the above description. The scope of the invention therefore should be determined with reference to the appended claims, along with the full scope of equivalents to which such claims are entitled. In the appended claims, the terms "including" and "in which" are used as the plain-English equivalents of the respective terms "comprising" and "wherein."

EXAMPLES

Cells and Reagents.

HEK293 cell line, prostate cancer cell line PC3, LNCaP, Du145, MDA-MB-231, and HCT116 cells were originally obtained from the American Type of Culture Collection (ATCC) and maintained in DMEM supplemented with 10% fetal bovine serum and 1% Penicillin/Streptomycin under 5% $CO_2$ at 37° C. Mouse anti-Flag-tag antibody (F1804), proteasome inhibitor MG231, and phlorizin dihydrate were obtained from Sigma-Aldrich (St. Louis, Mo.). AEE788, Gefitinib, and Erlotinib were obtained from Selleckchem (Houston, Tex.). Antibody against pEGFR (Y1173) (cat. no. 2434L) was obtained from Cell Signaling (Danvers, Mass.). Monoclonal antibody against C225 was obtained from Dr. Lee Elis (M.D. Anderson Cancer Center). Rabbit anti-actin (cat. no. sc-7210), rabbit anti-HA-tag antibody (sc-805), secondary antibodies against rabbit and mouse labeled with horseradish peroxidase, and protein A/G conjugated agarose beads (cat. no. sc-2003) were obtained from Santa Cruz Biotechnology (Santa Cruz, Calif.). MTT kit (cat.no.30-1010K) was obtained from ATCC. The plasmid expressing flag tagged human SGLT1 and the rabbit anti-human-SGLT1 polyclonal antibodies for immunohistochemical analysis (SGLT1-IHC) and Western blotting analysis (SGLT1-WB) have been previously described (Blessing A, et al., Sodium/Glucose Co-transporter 1 Expression Increases in Human Diseased Prostate, J. Cancer Sci. Ther. 4(9):306-312 (2012)).

Plasmid Constructions.

Human wild type EGFR was cloned into a pcDNA3.1 vector (Clontech, CA), which was used as a parental vector to generate all the other EGFR constructs. The pRK5 expression plasmid (Clontech, CA) with a c-terminal HA tag was used for the constructions of all HA tagged EGFRs. The full-length human EGFR was amplified with a forward primer EGFR-F (ATTCTCGAGCGGGGAGCAGCGATG) and a reverse primer EGFR-R (CCTAAGCTTTGCTCCAATAAATTCACTG). DNA fragments were digested by Xho I and Hind III and cloned into the corresponding sites of the pRK5 vector. Primers for cloning the EGFR with extracellular domain deletion (ΔExtra, 1-644aa) are ΔExtra-F: ATTCTCGAGATGTCC ATCGCCACTGGGATG and ΔExtra-R: CCTAAGCTTTGCTCCAATAAATTCACTGC; primers for intracellular deletion (ΔIntro, 671-1210 aa) are ΔIntra-F: TATCTCGAGATGCGACCCTCCGGGACGGC and ΔIntra-R: CCTAAGCTTCC TTCGCATGAAGAGGCC; primers for autophosphorylation domain deletion (ΔAutophos, 978-1210aa) are ΔAutophospho-F: ATTCTC-GAGATGTCCATCGCCACTGGGATG and ΔAutophospho-R: CCTAAGCTTG-TAGCGCTGGGGGTCTCGG; primers for intracellular domain deletion (645-1210aa) are ΔIntra-F: TATCTCGA-GATGCGACCCTCCGGGACGGC and ΔIntra-R: CCTAAGCTTCCTTCGCATGAAGAGGC. The kinase dead mutant of EGFR (KD-EGFR, R817M), transmembrane domain deletion (ΔTM, 645-670aa), and tyrosine kinase domain deletion (ΔTK, 670-977aa) plasmids were constructed from pRK5-WT-EGFR-HA by site-directed mutagenesis using the QuikChange Lightning Site-Directed Mutagenesis Kit (Agilent, CA) according to the manufacturer's protocol. The primers were: KD-EGFR-F: GCAC-CGCGACCTGGCAGCC ATGAACGTACTGGT-GAAAACACC and KD-EGFR-R: GGTGTTTTCACCAGTACGTTCATGGCTGCCA GGTCGCGGTGC; ΔTM-F: CGAGACCCCCAGCGC-TACCGGACTCCCCTCCTGAGC and ΔTM-R: CGA-GACCCCCAGCGCTACCGGACTCCCCTCCTGAGC; ΔTK-F: CGCTGCGGAGGCTGCTGCAGTAC CTTGT-CATTCAGGGGG and ΔTK-R: CCCCCTGAATGCAAGG-TACTGCAGCAGCCTCCGCAGCG. All of the constructs yielded fusion proteins with a C-terminal HA tag. All plasmids were confirmed by sequencing.

Transient Transfection and Immunoprecipitation.

HEK293 cells were transfected with plasmids expressing flagged SGLT1 alone or with indicated HA tagged EGFR constructs. After 24 hours of transfection, cells were washed in 1× phosphate buffered solution and lysed with RIPA buffer (50 mM Tris-HCl, pH 8.0, with 150 mM sodium chloride, 1.0% Igepal CA-630 (NP-40), 0.5% sodium deoxycholate, and 0.1% sodium dodecyl sulfate), supplemented with a protease inhibitors cocktail for 6 hours on a shaker at 4° C. The cell lysates were then centrifuged for 2 minutes at 12000× rpm. Supernatant were then incubated with sepharose protein A/G beads conjugated with anti-flag or anti-SGLT1 antibody for overnight at 4° C. Samples were then centrifuged and washed with RIPA buffer three times before boiled in Laemmle buffer (Biorad, CA) and subjected to Western blot analysis. To determine the role of EGFR's tyrosine kinase in EGFR-SGLT1 interaction, HEK293 cells were transfected with SGLT1 and wild type EGFR. After 18 h, cells were starved in serum free medium for 6 h before EGF treatment (10 ng/ml), or EGF plus AEE788 (5 μM) for 30-60 min. Control cells were treated with an equal volume of vehicle dimethyl sulfoxide (DMSO). Cell lysates were then subjected to immunoprecipitation as described above.

Western Blot Analysis.

For Western blot (WB) analysis, cells were lysed with RIPA buffer (150 mM NaCl, 50 mM Tris-HCl, pH 7.4, 0.1% SDS, 1% TritonX-100, 1 mM EDTA, 1 mM PMSF, 20 μg/ml aprotinin, 20 μg/ml leupeptin, 20 μg/ml pepstatine, 1% sodium deoxycholate, 1 mM NaF, 1 mM $Na_3VO_4$, in $H_2O$). Proteins separated by 8% SDS-PAGE were transferred to PVDF membrane followed by blocking with 5% nonfat dry milk and then incubation with primary antibodies at optimized concentrations for overnight at 4° C. The membranes were washed with 0.1% TBS/T (1×TBS, 0.1% Tween-20) 3 times, each time for 5 min before incubation with secondary antibody for 1 hour at room temperature. Signals were visualized by enhanced chemiluminescence.

Immunofluorescent Co-Staining.

For immunofluorescent co-staining of SGLT1 and EGFR, slides of prostate cancer tissue array were deparraffinated and rehydrated before antigens were retrieved in boiling citrate buffer for 10 min. Cooled tissue slides were then incubated in a blocking solution (5% donkey serum in PBS) for 1 hour at room temperature and then overnight at 4° C. with the rabbit polyclonal antibody against SGLT1 (SGLT1-IHC) (1:200 dilution) and C225 (1:200) in PBS containing 10% donkey serum (Blessing A, et al., Sodium/Glucose Cotransporter 1 Expression Increases in Human Diseased Prostate, J. Cancer Sci. Ther., 4(9):306-312 (2012)). After being washed three times with PBS, tissues were incubated with a mixture of Alexa Fluor 488—conjugated donkey anti-rabbit IgG and Alexa Flour 594—conjugated donkey anti-mouse IgG dissolved in PBS containing 10% donkey serum for 30 minutes at room temperature. The stained samples were then washed three times (5 minutes per wash) with PBS at room temperature. Fluorescence images were captured and analyzed with a confocal microscope (Olympus). Cell nucleus was stained by 4',6-diamidino-2-phenylindole (DAPI).

Cell Growth Assay.

Cell growth was determined by 3-(4,5-dimethylthiazole-2-yl)-2,5-diphenyltetrazolium Bromide (MTT) assay in 96-well plates according to the protocol provided by the manufacture. Briefly, 5000 cells suspended in 100 μL medium were seeded in each well of a 96-well plate. On the second day, medium was replaced by medium containing Phlozidin (50 μM) and EGFR inhibitors (Iressa: 20 μM; Erlotinib: 20 μM). After 24 or 48 hours incubation with drugs, 10 μL MTT reagents was added to each well and incubated for 4 hours. After removal of the medium, the formazan precipitates in cells were dissolved in 100 μL DMSO. Absorbance was measured by a MultiSkan plate reader (Thermo Fisher Scientific, NC) at 570 nm. Triplicates of sample in each group were used. Cell viability was determined by trypan blue uptake assay. The percentage of live cells were counted in areas (n=3 for each sample) randomly selected under 10× magnificence of triplicates.

Statistical Analysis.

The Student's t test was used to assess the difference in growth of cells treated with EGFR inhibitors in the presence/absence of SGLT1 inhibitor. P values less than 0.05 were defined as having statistical significance.

What is claimed is:

1. A method of treating cancer cells comprising:
identifying a subject having cancer cells that express an epidermal growth factor receptor (EGFR) protein and a sodium/glucose co-transporter 1 (SGLT1) protein;
treating the cancer cells by administering to the subject a peptide capable of destabilizing both EGFR and SGLT1 proteins, wherein the peptide consists of one of SEQ ID NO: 001, SEQ ID NO: 002, SEQ ID NO: 003, SEQ ID NO: 004, SEQ ID NO: 005, SEQ ID NO: 006, SEQ ID NO: 007, SEQ ID NO: 008, SEQ ID NO: 009, SEQ ID NO: 010, and SEQ ID NO: 011.

2. The method of claim 1, further comprising co-administering to the subject a tyrosine-kinase inhibitor with the peptide.

3. The method of claim 1, wherein the peptide is administered to cause the death of cancer cells.

4. The method of claim 1, wherein the cancer cells include at least one of breast cancer cells, prostate cancer cells, and colon cancer cells.

5. The method of claim 2, wherein the tyrosine-kinase inhibitor is at least one of Gefitnib, Erlotinib, Icontinib, Mubritinib, Vandertanib, Lapatinib, Peletinib, Canetinib, Neratinib, Afatinib, and Dacomitinib.

6. The method of claim 1, wherein the cancer cells are at least one of breast cancer cells, prostate cancer cells, colon cancer cells, ovarian cancer cells, oral squamous cancer cells, and pancreatic cancer cells.

* * * * *

UNITED STATES PATENT AND TRADEMARK OFFICE
CERTIFICATE OF CORRECTION

PATENT NO. : 9,770,482 B2
APPLICATION NO. : 15/139066
DATED : September 26, 2017
INVENTOR(S) : Zhang Weihua Page 1 of 1

It is certified that error appears in the above-identified patent and that said Letters Patent is hereby corrected as shown below:

In the Specification

Column 1, Lines 15-17 - Replace:
"American Cancer Society (RSG-09-206-01) and Department of Defense Prostate Cancer Research Program (W91ZSQ8334N607)"

With:
-- This invention was made with government support under Grant number W81XWH-09-1-0343 awarded by the Defense Health Agency, Medical Research and Development Branch, and Grant number RSG-09-206-01 awarded by the American Cancer Society. The government has certain rights in the invention. --

Signed and Sealed this
Twenty-fourth Day of June, 2025

Coke Morgan Stewart
*Acting Director of the United States Patent and Trademark Office*

SEQUENCE LISTING

```
<160> NUMBER OF SEQ ID NOS: 17

<210> SEQ ID NO 1
<211> LENGTH: 14
<212> TYPE: PRT
<213> ORGANISM: Homo sapiens

<400> SEQUENCE: 1

Leu Val Trp Lys Gln Ser Cys Ser Ser Thr Ser Ser Thr His
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Serine (S) in ESD-01 can be substituted with
      Threonine (T), Tyrosine (Y), or any other non-natural hydroxyl
      containing amino acid
<220> FEATURE:
<221> NAME/KEY: MISC_FEATURE
<222> LOCATION: (8)..(8)
<223> OTHER INFORMATION: Serine (S) in ESD-01 can be substituted with
      Threonine (T), Tyrosine (Y), or any other non-natural hydroxyl
      containing amino acid
<220> FEATURE:
<221> NAME/KEY: MISC_FEATURE
<222> LOCATION: (9)..(9)
<223> OTHER INFORMATION: Serine (S) in ESD-01 can be substituted with
      Threonine (T), Tyrosine (Y), or any other non-natural hydroxyl
      containing amino acid
<220> FEATURE:
<221> NAME/KEY: MISC_FEATURE
<222> LOCATION: (11)..(11)
<223> OTHER INFORMATION: Serine (S) in ESD-01 can be substituted with
      Threonine (T), Tyrosine (Y), or any other non-natural hydroxyl
      containing amino acid
<220> FEATURE:
<221> NAME/KEY: MISC_FEATURE
<222> LOCATION: (12)..(12)
<223> OTHER INFORMATION: Serine (S) in ESD-01 can be substituted with
      Threonine (T), Tyrosine (Y), or any other non-natural hydroxyl
      containing amino acid

<400> SEQUENCE: 2

Leu Val Trp Lys Gln Xaa Cys Xaa Xaa Thr Xaa Xaa Thr His
```

<210> SEQ ID NO 3
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Threonine (T) in ESD-01 can be substituted
      with Serine (S), Tyrosine (Y), or any other non-natural hydroxyl
      containing amino acid
<220> FEATURE:
<221> NAME/KEY: MISC_FEATURE
<222> LOCATION: (13)..(13)
<223> OTHER INFORMATION: Threonine (T) in ESD-01 can be substituted with
      Serine (S), Tyrosine (Y), or any other non-natural hydroxyl
      containing amino acid

<400> SEQUENCE: 3

Leu Val Trp Lys Gln Ser Cys Ser Ser Xaa Ser Ser Xaa His
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic

<400> SEQUENCE: 4

Leu Val Trp Thr Gln Ser Cys Ser Ser Thr Ser Ser Thr His
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic

<400> SEQUENCE: 5

Leu Val Trp Lys His Ser Cys Ser Ser Thr Ser Ser Thr His
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic

<400> SEQUENCE: 6

Leu Val Trp Lys Gln Ser Cys Ser Ser Ala Ser Ser Thr His
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic

<400> SEQUENCE: 7

Leu Val Trp Lys Gln Ser Cys Ser Ser Thr Ser Leu Thr His
1               5                   10

```
<210> SEQ ID NO 8
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: the polar positive charged amino acids Lysine
      (K) can be any other natural and non-natural positively charged
      amino acid
<220> FEATURE:
<221> NAME/KEY: MISC_FEATURE
<222> LOCATION: (4)..(4)
<223> OTHER INFORMATION: the polar positive charged amino acid Lysine
      (K) can be any other natural and non-natural positively charged
      amino acid
<220> FEATURE:
<221> NAME/KEY: MISC_FEATURE
<222> LOCATION: (14)..(14)
<223> OTHER INFORMATION: the polar positive charged amino acid Histidine
      (H) can be any other natural and non-natural positively charged
      amino acid

<400> SEQUENCE: 8

Leu Val Trp Xaa Gln Ser Cys Ser Ser Thr Ser Ser Thr Xaa
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: the Glutamine (Q) can be any other natural and
      non-natural polar amino acid
<220> FEATURE:
<221> NAME/KEY: MISC_FEATURE
<222> LOCATION: (7)..(7)
<223> OTHER INFORMATION: the polar amino acid Cysteine (C) can be any
      other natural and non-natural polar amino acid

<400> SEQUENCE: 9

Leu Val Trp Lys Xaa Ser Xaa Ser Ser Thr Ser Ser Thr His
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: the Cysteine (C) in ESD-01 can be any other
      natural and non-natural thiol side chain (-SH) containing amino
      acid, such as for one example, homocysteine

<400> SEQUENCE: 10

Leu Val Trp Lys Gln Ser Xaa Ser Ser Thr Ser Ser Thr His
1               5                   10

<210> SEQ ID NO 11
<211> LENGTH: 14
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (1)..(3)
<223> OTHER INFORMATION: the nonpolar amino acids in ESD-01, Leucine
      (L), Valine (V), and Tryptophan (W), can be any other natural and
      non-natural nonpolar amino acids

<400> SEQUENCE: 11

Xaa Xaa Xaa Lys Gln Ser Cys Ser Ser Thr Ser Ser Thr His
1               5                   10

<210> SEQ ID NO 12
<211> LENGTH: 1210
<212> TYPE: PRT
<213> ORGANISM: Artificial Sequence
<220> FEATURE:
<223> OTHER INFORMATION: Synthetic

<400> SEQUENCE: 12

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300
```

```
Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
            325                 330                 335

Cys Asn Gly Ile Gly Ile Gly Glu Phe Lys Asp Ser Leu Ser Ile Asn
        340                 345                 350

Ala Thr Asn Ile Lys His Phe Lys Asn Cys Thr Ser Ile Ser Gly Asp
    355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720
```

```
Gly Ala Phe Gly Thr Val Tyr Lys Gly Leu Trp Ile Pro Glu Glu
            725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Met Asn Val Leu Val Lys Thr Pro
                835                 840                 845

Gln His Val Lys Ile Thr Asp Phe Gly Leu Ala Lys Leu Leu Gly Ala
            850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
            995                 1000                1005

Asp Val  Val Asp Ala Asp Glu  Tyr Leu Ile Pro Gln  Gln Gly Phe
            1010                1015                1020

Phe Ser  Ser Pro Ser Thr Ser  Arg Thr Pro Leu Leu  Ser Ser Leu
            1025                1030                1035

Ser Ala  Thr Ser Asn Asn Ser  Thr Val Ala Cys Ile  Asp Arg Asn
            1040                1045                1050

Gly Leu  Gln Ser Cys Pro Ile  Lys Glu Asp Ser Phe  Leu Gln Arg
            1055                1060                1065

Tyr Ser  Ser Asp Pro Thr Gly  Ala Leu Thr Glu Asp  Ser Ile Asp
            1070                1075                1080

Asp Thr  Phe Leu Pro Val Pro  Glu Tyr Ile Asn Gln  Ser Val Pro
            1085                1090                1095

Lys Arg  Pro Ala Gly Ser Val  Gln Asn Pro Val Tyr  His Asn Gln
            1100                1105                1110

Pro Leu  Asn Pro Ala Pro Ser  Arg Asp Pro His Tyr  Gln Asp Pro
            1115                1120                1125

His Ser  Thr Ala Val Gly Asn  Pro Glu Tyr Leu Asn  Thr Val Gln
```

```
                1130                1135                1140
Pro Thr Cys Val Asn Ser Thr Phe Asp Ser Pro Ala His Trp Ala
    1145                1150                1155
Gln Lys Gly Ser His Gln Ile Ser Leu Asp Asn Pro Asp Tyr Gln
    1160                1165                1170
Gln Asp Phe Phe Pro Lys Glu Ala Lys Pro Asn Gly Ile Phe Lys
    1175                1180                1185
Gly Ser Thr Ala Glu Asn Ala Glu Tyr Leu Arg Val Ala Pro Gln
    1190                1195                1200
Ser Ser Glu Phe Ile Gly Ala
    1205            1210

<210> SEQ ID NO 13
<211> LENGTH: 1184
<212> TYPE: PRT
<213> ORGANISM: Artificial Sequence
<220> FEATURE:
<223> OTHER INFORMATION: Synthetic

<400> SEQUENCE: 13

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
```

```
            275                 280                 285
Ala Thr Cys Val Lys Lys Cys Pro Arg Asn Tyr Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
            610                 615                 620

Thr Tyr Gly Cys Thr Gly Pro Gly Leu Glu Gly Cys Pro Thr Asn Gly
625                 630                 635                 640

Pro Lys Ile Pro Arg His Ile Val Arg Lys Arg Thr Leu Arg Arg Leu
                645                 650                 655

Leu Gln Glu Arg Glu Leu Val Glu Pro Leu Thr Pro Ser Gly Glu Ala
                660                 665                 670

Pro Asn Gln Ala Leu Leu Arg Ile Leu Lys Glu Thr Glu Phe Lys Lys
            675                 680                 685

Ile Lys Val Leu Gly Ser Gly Ala Phe Gly Thr Val Tyr Lys Gly Leu
            690                 695                 700
```

```
Trp Ile Pro Glu Gly Glu Lys Val Lys Ile Pro Val Ala Ile Lys Glu
705                 710                 715                 720

Leu Arg Glu Ala Thr Ser Pro Lys Ala Asn Lys Glu Ile Leu Asp Glu
            725                 730                 735

Ala Tyr Val Met Ala Ser Val Asp Asn Pro His Val Cys Arg Leu Leu
                740                 745                 750

Gly Ile Cys Leu Thr Ser Thr Val Gln Leu Ile Thr Gln Leu Met Pro
            755                 760                 765

Phe Gly Cys Leu Leu Asp Tyr Val Arg Glu His Lys Asp Asn Ile Gly
        770                 775                 780

Ser Gln Tyr Leu Leu Asn Trp Cys Val Gln Ile Ala Lys Gly Met Asn
785                 790                 795                 800

Tyr Leu Glu Asp Arg Arg Leu Val His Arg Asp Leu Ala Ala Arg Asn
                805                 810                 815

Val Leu Val Lys Thr Pro Gln His Val Lys Ile Thr Asp Phe Gly Leu
            820                 825                 830

Ala Lys Leu Leu Gly Ala Glu Glu Lys Glu Tyr His Ala Glu Gly Gly
        835                 840                 845

Lys Val Pro Ile Lys Trp Met Ala Leu Glu Ser Ile Leu His Arg Ile
850                 855                 860

Tyr Thr His Gln Ser Asp Val Trp Ser Tyr Gly Val Thr Val Trp Glu
865                 870                 875                 880

Leu Met Thr Phe Gly Ser Lys Pro Tyr Asp Gly Ile Pro Ala Ser Glu
                885                 890                 895

Ile Ser Ser Ile Leu Glu Lys Gly Glu Arg Leu Pro Gln Pro Pro Ile
            900                 905                 910

Cys Thr Ile Asp Val Tyr Met Ile Met Val Lys Cys Trp Met Ile Asp
        915                 920                 925

Ala Asp Ser Arg Pro Lys Phe Arg Glu Leu Ile Ile Glu Phe Ser Lys
        930                 935                 940

Met Ala Arg Asp Pro Gln Arg Tyr Leu Val Ile Gln Gly Asp Glu Arg
945                 950                 955                 960

Met His Leu Pro Ser Pro Thr Asp Ser Asn Phe Tyr Arg Ala Leu Met
                965                 970                 975

Asp Glu Glu Asp Met Asp Asp Val Val Asp Ala Asp Glu Tyr Leu Ile
            980                 985                 990

Pro Gln Gln Gly Phe Phe Ser Ser Pro Ser Thr Ser Arg Thr Pro Leu
        995                 1000                1005

Leu Ser Ser Leu Ser Ala Thr Ser Asn Asn Ser Thr Val Ala Cys
    1010                1015                1020

Ile Asp Arg Asn Gly Leu Gln Ser Cys Pro Ile Lys Glu Asp Ser
    1025                1030                1035

Phe Leu Gln Arg Tyr Ser Ser Asp Pro Thr Gly Ala Leu Thr Glu
    1040                1045                1050

Asp Ser Ile Asp Asp Thr Phe Leu Pro Val Pro Glu Tyr Ile Asn
    1055                1060                1065

Gln Ser Val Pro Lys Arg Pro Ala Gly Ser Val Gln Asn Pro Val
    1070                1075                1080

Tyr His Asn Gln Pro Leu Asn Pro Ala Pro Ser Arg Asp Pro His
    1085                1090                1095

Tyr Gln Asp Pro His Ser Thr Ala Val Gly Asn Pro Glu Tyr Leu
    1100                1105                1110
```

```
Asn Thr Val Gln Pro Thr Cys Val Asn Ser Thr Phe Asp Ser Pro
    1115                1120                1125

Ala His Trp Ala Gln Lys Gly Ser His Gln Ile Ser Leu Asp Asn
    1130                1135                1140

Pro Asp Tyr Gln Gln Asp Phe Phe Pro Lys Glu Ala Lys Pro Asn
    1145                1150                1155

Gly Ile Phe Lys Gly Ser Thr Ala Glu Asn Ala Glu Tyr Leu Arg
    1160                1165                1170

Val Ala Pro Gln Ser Ser Glu Phe Ile Gly Ala
    1175                1180

<210> SEQ ID NO 14
<211> LENGTH: 566
<212> TYPE: PRT
<213> ORGANISM: Artificial Sequence
<220> FEATURE:
<223> OTHER INFORMATION: Synthetic

<400> SEQUENCE: 14

Ser Ile Ala Thr Gly Met Val Gly Ala Leu Leu Leu Leu Val Val
1               5                   10                  15

Ala Leu Gly Ile Gly Leu Phe Met Arg Arg Arg His Ile Val Arg Lys
            20                  25                  30

Arg Thr Leu Arg Arg Leu Leu Gln Glu Arg Glu Leu Val Glu Pro Leu
        35                  40                  45

Thr Pro Ser Gly Glu Ala Pro Asn Gln Ala Leu Leu Arg Ile Leu Lys
    50                  55                  60

Glu Thr Glu Phe Lys Lys Ile Lys Val Leu Gly Ser Gly Ala Phe Gly
65                  70                  75                  80

Thr Val Tyr Lys Gly Leu Trp Ile Pro Glu Gly Glu Lys Val Lys Ile
                85                  90                  95

Pro Val Ala Ile Lys Glu Leu Arg Glu Ala Thr Ser Pro Lys Ala Asn
            100                 105                 110

Lys Glu Ile Leu Asp Glu Ala Tyr Val Met Ala Ser Val Asp Asn Pro
        115                 120                 125

His Val Cys Arg Leu Leu Gly Ile Cys Leu Thr Ser Thr Val Gln Leu
    130                 135                 140

Ile Thr Gln Leu Met Pro Phe Gly Cys Leu Leu Asp Tyr Val Arg Glu
145                 150                 155                 160

His Lys Asp Asn Ile Gly Ser Gln Tyr Leu Leu Asn Trp Cys Val Gln
                165                 170                 175

Ile Ala Lys Gly Met Asn Tyr Leu Glu Asp Arg Arg Leu Val His Arg
            180                 185                 190

Asp Leu Ala Ala Arg Asn Val Leu Val Lys Thr Pro Gln His Val Lys
        195                 200                 205

Ile Thr Asp Phe Gly Leu Ala Lys Leu Leu Gly Ala Glu Glu Lys Glu
    210                 215                 220

Tyr His Ala Glu Gly Gly Lys Val Pro Ile Lys Trp Met Ala Leu Glu
225                 230                 235                 240

Ser Ile Leu His Arg Ile Tyr Thr His Gln Ser Asp Val Trp Ser Tyr
                245                 250                 255

Gly Val Thr Val Trp Glu Leu Met Thr Phe Gly Ser Lys Pro Tyr Asp
            260                 265                 270

Gly Ile Pro Ala Ser Glu Ile Ser Ser Ile Leu Glu Lys Gly Glu Arg
        275                 280                 285
```

```
Leu Pro Gln Pro Pro Ile Cys Thr Ile Asp Val Tyr Met Ile Met Val
    290                 295                 300

Lys Cys Trp Met Ile Asp Ala Asp Ser Arg Pro Lys Phe Arg Glu Leu
305                 310                 315                 320

Ile Ile Glu Phe Ser Lys Met Ala Arg Asp Pro Gln Arg Tyr Leu Val
                325                 330                 335

Ile Gln Gly Asp Glu Arg Met His Leu Pro Ser Pro Thr Asp Ser Asn
            340                 345                 350

Phe Tyr Arg Ala Leu Met Asp Glu Asp Met Asp Asp Val Val Asp
        355                 360                 365

Ala Asp Glu Tyr Leu Ile Pro Gln Gln Gly Phe Phe Ser Ser Pro Ser
370                 375                 380

Thr Ser Arg Thr Pro Leu Leu Ser Ser Leu Ser Ala Thr Ser Asn Asn
385                 390                 395                 400

Ser Thr Val Ala Cys Ile Asp Arg Asn Gly Leu Gln Ser Cys Pro Ile
                405                 410                 415

Lys Glu Asp Ser Phe Leu Gln Arg Tyr Ser Ser Asp Pro Thr Gly Ala
            420                 425                 430

Leu Thr Glu Asp Ser Ile Asp Asp Thr Phe Leu Pro Val Pro Glu Tyr
        435                 440                 445

Ile Asn Gln Ser Val Pro Lys Arg Pro Ala Gly Ser Val Gln Asn Pro
450                 455                 460

Val Tyr His Asn Gln Pro Leu Asn Pro Ala Pro Ser Arg Asp Pro His
465                 470                 475                 480

Tyr Gln Asp Pro His Ser Thr Ala Val Gly Asn Pro Glu Tyr Leu Asn
                485                 490                 495

Thr Val Gln Pro Thr Cys Val Asn Ser Thr Phe Asp Ser Pro Ala His
            500                 505                 510

Trp Ala Gln Lys Gly Ser His Gln Ile Ser Leu Asp Asn Pro Asp Tyr
        515                 520                 525

Gln Gln Asp Phe Phe Pro Lys Glu Ala Lys Pro Asn Gly Ile Phe Lys
    530                 535                 540

Gly Ser Thr Ala Glu Asn Ala Glu Tyr Leu Arg Val Ala Pro Gln Ser
545                 550                 555                 560

Ser Glu Phe Ile Gly Ala
                565

<210> SEQ ID NO 15
<211> LENGTH: 670
<212> TYPE: PRT
<213> ORGANISM: Artificial Sequence
<220> FEATURE:
<223> OTHER INFORMATION: Synthetic

<400> SEQUENCE: 15

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80
```

```
Thr Ile Gln Glu Val Ala Gly Tyr Val Leu Ile Ala Leu Asn Thr Val
                85                  90                  95
Glu Arg Ile Pro Leu Glu Asn Leu Gln Ile Ile Arg Gly Asn Met Tyr
            100                 105                 110
Tyr Glu Asn Ser Tyr Ala Leu Ala Val Leu Ser Asn Tyr Asp Ala Asn
            115                 120                 125
Lys Thr Gly Leu Lys Glu Leu Pro Met Arg Asn Leu Gln Glu Ile Leu
130                 135                 140
His Gly Ala Val Arg Phe Ser Asn Asn Pro Ala Leu Cys Asn Val Glu
145                 150                 155                 160
Ser Ile Gln Trp Arg Asp Ile Val Ser Ser Asp Phe Leu Ser Asn Met
                165                 170                 175
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Asn Cys Gln
            195                 200                 205
Lys Leu Thr Lys Ile Ile Cys Ala Gln Gln Cys Ser Gly Arg Cys Arg
210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
            275                 280                 285
Ala Thr Cys Val Lys Lys Cys Pro Arg Asn Tyr Val Val Thr Asp His
290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
            355                 360                 365
Leu His Ile Leu Pro Val Ala Phe Arg Gly Asp Ser Phe Thr His Thr
370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
```

```
                500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
    595                 600                 605
Lys Tyr Ala Asp Ala Gly His Val Cys His Leu Cys His Pro Asn Cys
610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg
            660                 665                 670

<210> SEQ ID NO 16
<211> LENGTH: 902
<212> TYPE: PRT
<213> ORGANISM: Artificial Sequence
<220> FEATURE:
<223> OTHER INFORMATION: Synthetic

<400> SEQUENCE: 16

Met Arg Pro Ser Gly Thr Ala Gly Ala Ala Leu Leu Ala Leu Leu Ala
1               5                   10                  15
Ala Leu Cys Pro Ala Ser Arg Ala Leu Glu Glu Lys Lys Val Cys Gln
            20                  25                  30
Gly Thr Ser Asn Lys Leu Thr Gln Leu Gly Thr Phe Glu Asp His Phe
        35                  40                  45
Leu Ser Leu Gln Arg Met Phe Asn Asn Cys Glu Val Val Leu Gly Asn
50                  55                  60
Leu Glu Ile Thr Tyr Val Gln Arg Asn Tyr Asp Leu Ser Phe Leu Lys
65                  70                  75                  80
Thr Ile Gln Glu Val Ala Gly Tyr Val Leu Ile Ala Leu Asn Thr Val
                85                  90                  95
Glu Arg Ile Pro Leu Glu Asn Leu Gln Ile Ile Arg Gly Asn Met Tyr
            100                 105                 110
Tyr Glu Asn Ser Tyr Ala Leu Ala Val Leu Ser Asn Tyr Asp Ala Asn
        115                 120                 125
Lys Thr Gly Leu Lys Glu Leu Pro Met Arg Asn Leu Gln Glu Ile Leu
    130                 135                 140
His Gly Ala Val Arg Phe Ser Asn Asn Pro Ala Leu Cys Asn Val Glu
145                 150                 155                 160
Ser Ile Gln Trp Arg Asp Ile Val Ser Ser Asp Phe Leu Ser Asn Met
                165                 170                 175
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Glu Asn Cys Gln
```

```
                195                 200                 205
Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
610                 615                 620
```

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
            645                 650                 655

Leu Leu Val Val Ala Leu Gly Ile Gly Leu Phe Met Arg Tyr Leu Val
            660                 665                 670

Ile Gln Gly Asp Glu Arg Met His Leu Pro Ser Pro Thr Asp Ser Asn
            675                 680                 685

Phe Tyr Arg Ala Leu Met Asp Glu Glu Asp Met Asp Asp Val Val Asp
            690                 695                 700

Ala Asp Glu Tyr Leu Ile Pro Gln Gln Gly Phe Phe Ser Ser Pro Ser
705                 710                 715                 720

Thr Ser Arg Thr Pro Leu Leu Ser Ser Leu Ser Ala Thr Ser Asn Asn
            725                 730                 735

Ser Thr Val Ala Cys Ile Asp Arg Asn Gly Leu Gln Ser Cys Pro Ile
            740                 745                 750

Lys Glu Asp Ser Phe Leu Gln Arg Tyr Ser Ser Asp Pro Thr Gly Ala
            755                 760                 765

Leu Thr Glu Asp Ser Ile Asp Asp Thr Phe Leu Pro Val Pro Glu Tyr
            770                 775                 780

Ile Asn Gln Ser Val Pro Lys Arg Pro Ala Gly Ser Val Gln Asn Pro
785                 790                 795                 800

Val Tyr His Asn Gln Pro Leu Asn Pro Ala Pro Ser Arg Asp Pro His
            805                 810                 815

Tyr Gln Asp Pro His Ser Thr Ala Val Gly Asn Pro Glu Tyr Leu Asn
            820                 825                 830

Thr Val Gln Pro Thr Cys Val Asn Ser Thr Phe Asp Ser Pro Ala His
            835                 840                 845

Trp Ala Gln Lys Gly Ser His Gln Ile Ser Leu Asp Asn Pro Asp Tyr
850                 855                 860

Gln Gln Asp Phe Phe Pro Lys Glu Ala Lys Pro Asn Gly Ile Phe Lys
865                 870                 875                 880

Gly Ser Thr Ala Glu Asn Ala Glu Tyr Leu Arg Val Ala Pro Gln Ser
            885                 890                 895

Ser Glu Phe Ile Gly Ala
            900

<210> SEQ ID NO 17
<211> LENGTH: 978
<212> TYPE: PRT
<213> ORGANISM: Artificial Sequence
<220> FEATURE:
<223> OTHER INFORMATION: Synthetic

<400> SEQUENCE: 17

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

-continued

```
Thr Ile Gln Glu Val Ala Gly Tyr Val Leu Ile Ala Leu Asn Thr Val
                 85                  90                  95
Glu Arg Ile Pro Leu Glu Asn Leu Gln Ile Ile Arg Gly Asn Met Tyr
            100                 105                 110
Tyr Glu Asn Ser Tyr Ala Leu Ala Val Leu Ser Asn Tyr Asp Ala Asn
            115                 120                 125
Lys Thr Gly Leu Lys Glu Leu Pro Met Arg Asn Leu Gln Glu Ile Leu
130                 135                 140
His Gly Ala Val Arg Phe Ser Asn Asn Pro Ala Leu Cys Asn Val Glu
145                 150                 155                 160
Ser Ile Gln Trp Arg Asp Ile Val Ser Ser Asp Phe Leu Ser Asn Met
                165                 170                 175
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Glu Asn Cys Gln
            195                 200                 205
Lys Leu Thr Lys Ile Ile Cys Ala Gln Gln Cys Ser Gly Arg Cys Arg
210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
            275                 280                 285
Ala Thr Cys Val Lys Lys Cys Pro Arg Asn Tyr Val Val Thr Asp His
290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
            355                 360                 365
Leu His Ile Leu Pro Val Ala Phe Arg Gly Asp Ser Phe Thr His Thr
370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
```

-continued

```
Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
```

-continued

```
            915                 920                 925
Lys Gly Glu Arg Leu Pro Gln Pro Pro Ile Cys Thr Ile Asp Val Tyr
        930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr
```